(12) United States Patent
Takano et al.

(10) Patent No.: US 7,217,511 B2
(45) Date of Patent: May 15, 2007

(54) **METHODS OF INCREASING ANTIBIOTIC PRODUCTION IN *STREPTOMYCES* BY DELETION OF THE SCBA GENE**

(75) Inventors: Eriko Takano, Norwich (GB); Mervyn J. Bibb, San Diego, CA (US)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 10/017,471

(22) Filed: Oct. 23, 2001

(65) Prior Publication Data

US 2003/0124644 A1 Jul. 3, 2003

Related U.S. Application Data

(60) Provisional application No. 60/242,561, filed on Oct. 23, 2000.

(51) Int. Cl.
*C12Q 1/68* (2006.01)
*C12N 1/20* (2006.01)
*C12N 15/76* (2006.01)

(52) U.S. Cl. .................. 435/6; 435/471; 435/486; 435/252.35; 536/23.7; 536/23.1

(58) Field of Classification Search ............... 435/471, 435/252.35, 4
See application file for complete search history.

(56) References Cited

OTHER PUBLICATIONS

Kawachi et al. Identification of an AfsA homologue (BarX) from *Streptomyces virginiae* as a pleiotropic regulator controlling autoregulator biosynthesis, virginiamycin biosynthesis and virginiamycin M1 resistance. Mol Microbiol (Apr., 2000) 36:302-313.*
Takano et al. A complex role for the gamma-butyrolactone SCB1 in regulating antibiotic production in *Streptomyces coelicolor* A3(2). Molecular Microbiology (2001) 41(5):1015-1028.*
Butler et al. Deletion of scbA enhances antibiotic production in *Streptomyces lividans*. Appl. Microbiol. Biotechnol. (2003) 61:512-516.*
GenBank Accession No. NP_823445. putative gamma-butyrolactone biosynthesis protein [*Streptomyces avermitilis* MA-4680] (2004).*
Ando, N., et al., "Involvement of AfsA in A-factor Biosynthesis as a Key Enzyme", J. Antibiot. 50: 847-852, (1997).
Bate, N., et al., "Multiple regulatory genes in the tylosin biosynthetic cluster of *Streptomyces fradiae*", Chemistry & Biology, 6: 617-624, (1999).
Fouces, R., et al., "The tylosin biosynthetic cluster from *Streptomyces fradiae*: genetic organization of the left region", Microbiology, 145: 855-868, (1999).
Gramajo, H.C., et al., "Stationary-phase production of the antibiotic actinorhodin in *Streptomyces coelicolor* A3(2) is transcriptionally regulated", Mol. Microbiol., 7: 837-845, (1993).
Hara, O., et al., "Genetic Analysis of A-factor Synthesis in *Streptomyces coelicolor* A3(2) and *Streptomyces griseus*", J. Gen. Microbiol., 129: 2939-2944, (1983).

Hopwood, D.A., et al., "Genetics of Antibiotic Production in *Streptomyces coelicolor* A3(2), a Model *Streptomycete*", In: Genetics and Biochemistry of Antibiotic Production, Vining, L. (ed), Butterworth-Heinemann, Newton, MA, USA, pp. 65-102 (1985).
Hourinouchi, S., and Beppu, T., Autoregulators. In: Genetics and Biochemistry of Antibiotic Production. Vining, L. (ed) Butterworth-Heinemann, Newton, MA, USA. pp. 103-119, (1994).
Horinouchi, S., et al., "The Cloned *Steptomyces* Bikiniensis A-Factor Determinant", J. Antibiot., 36: 636-641, (1985).
Horinouchi, S., et al., "Nucleotide Sequence and Transcriptional Analysis of the *Streptomyces griseus* Gene (afsA) Responsible for A-Factor Biosynthesis", J. Bacteriol., 171: 1206-1210, (1989).
Ikeda, H., et al., "Organization of the biosynthetic gene cluster for the polyketide anthelmintic macrolide avermectin in *Streptomyces avermitilis*", Proc. Natl. Acad. Sci. 17: 9509-9514, (1999).
Kieser, H.M., et al., "A Combined Genetic and Physical Map of the *Streptomyces coelicolor* A3(2) Chromosome", J. Bacteriol. 174: 5496-5507, (1992).
Kim, H.S., et al., "Identification of binding protein of Virginiae butanolide C, an autoregulator in Virginiamycin production, from *Streptomyces Virginiae*", J. Antibiot., 42: 769-778, (1989).
Kinoshita, H., et al., "Butyrolactone Autoregulator Receptor Protein (BarA) as a Transcriptional Regulator in *Streptomyces virginiae*", J. Bacteriol. 179: 6989-93, (1997).
Kitani, S., et al., "In vitro analysis of the butyrolactone autoregulator receptor protein (FarA) of *Streptomyces lavendulae* FRI-5 reveals that FarA as a DNA-binding transcriptional regulator that controls its own synthesis", J. Bacteriol., 181: 5081-5084, (1999).
Lezhava, A., et al., "Chromosomal deletions in *Streptomyces griseus* that remove the afsA locus", Mol. Gen. Genet. 253: 478-483, (1997).
Miyake, K., et al., "The A-factor-binding protein of *Streptomyces griseus* negatively controls *Streptomycin* production and sporulation", J. Bacteriol., 172: 3003-3008, (1990).
Mori, K., "Revision of the absolute configuration of A-factor", Tetrahedron Lett. 39: 3107-3109, (1983).
Nakano, H., et al., "Gene replacement analysis of the *Streptomyces virginiae* barA gene encoding the butyrolactone autoregulator receptor that barA acts as a repressor in *Virginiamycin biosynthesis*", J. Bacteriol., 180: 3317-3322, (1998).

(Continued)

*Primary Examiner*—Nashaat T. Nashed
(74) *Attorney, Agent, or Firm*—Dann, Dorfman, Herrell & Skillman, P.C.

(57) ABSTRACT

Methods are provided for increasing and altering the timing of antibiotic production in *Streptomyces* species, particularly *S. coelicolor* and *S. lividans*, by functionally deleting the *S. coelicolor* scbA and scbR genes, respectively, or their homologues. Also provided are strains having such mutations, and methods of producing antibiotics using such strains. Also provided are methods for identifying strains in which functional deletion of the scbA and/or scbR genes or their homologues leads to the above effects.

9 Claims, 19 Drawing Sheets

OTHER PUBLICATIONS

Nihira, T., et al., "Structure-activity relationships of *Virginiae butanolide* C, an inducer of *Virginiamycin* production in *Streptomyces Virginiae*", J. Antibiot., 41: 1828-1837, (1988).

Okamoto, S., et al., "*Virginiae butanolide* binding protein from *Streptomyces virginiae*", J. Biol. Chem., 270: 12319-12326, (1995).

Onaka, H., et al., "Cloning and characterization of the A-Factor receptor gene from *Streptomyces griseus*", J. Bacteriol., 177: 6083-6092, (1995).

Onaka, H., et al., "DNA-binding activity of the A-factor receptor protein and its recognition DNA sequences", Mol. Microbiol., 24: 991-1000, (1997).

Onaka, H., et al., "Involvement of two A-factor receptor homologues in *Streptomyces coelicolor* A3(2) in the regulation of secondary metabolism and morphogenesis", Mol. Microbiol. 28: 743-753, (1998).

Ohnishi, Y., et al., "The A-factor regulatory cascade leading to *streptomycin biosynthesis* in *Streptomyces griseus*: identification of a target gene of the A-factor receptor", Mol. Microbiol., 34: 102-111, (1999).

Redenbach, M., et al., "A set of ordered cosmids and a detailed genetic and physical map for the 8 Mb *Streptomyces coelicolor* A3(2) chromosome", Mol. Microbiol., 21: 77-95, (1996).

Ruengjitchatchawalya, M., et al., "Purification and characterization of the IM-2-binding protein from *Streptomyces sp.* strain FRI-5", J. Bacteriol., 177: 551-557, (1995).

Sato, K., et al., "Isolation and structure of a new butyrolactone autoregulator from *Streptomyces sp.* FRI-5", J. Ferment Bioeng., 68: 170-173, (1989).

Takano, E., et al., "Transcriptional regulation of the redD transcriptional activator gene accounts for growth-phase-dependent production of the antibiotic undeclyprodigiosin in *Streptomyces coelicolor* A3(2)", Mol. Microbiol., 6: 2729-2804, (1992).

Takano, E., et al., "Purification and structural determination of SCB1, a γ-butyrolactone that elictis antibiotic production in *Streptomyces coelicolor* A3(2)", J. Biol. Chem., 275: 11010-11016, (2000).

Waki, M., et al., "Cloning and characterization of the gene (farA) encoding that receptor for an extracellular regulatory factor (IM-2) from *Streptomyces sp.* strain FRI-5", J. Bacteriol., 179(16): 5131-5137, (1997).

Yamada, Y., "Autoregulatory factors and regulation of antibiotic production in *Streptomyces*", In Microbial singalling and communication. England, R., Hobbs, G., Bainton, N., and Roberts, D. McL. (eds.) Cambridge: the Society for General Microbiology, pp. 177-196, (1999).

Yamada, Y., et al., "The structure of inducing factors for *Virginiamycin* production in *Streptomyces virginiae*", J. Antibiot., 40: 496-504, (1987).

Passantio, R., et al., "Additional copies of the actII regulatory gene induce actinorhodin production in pleiotropic bld mutants of *Streptomyces coelicolor* A3(2)", J. Gen. Microbiol., 137: 2059-2064, (1991).

Aigle, B., et al., "A single amino acid substitution in region 1.2 of the principal α factor of *Streptomyces coelicolor* A3(2) results in pleiotropic loss of antibiotic production", Mol. Microbiol., 37 (5): 995-1004 (2000).

Sugiyama, M., et al., "Site-directed mutagenesis of the A-factor receptor protein: Val-41 important for DNA-binding and Trp-119 important for ligand-binding", Gene, 222(1): 133-44, (1998).

\* cited by examiner

Fig. 2 A
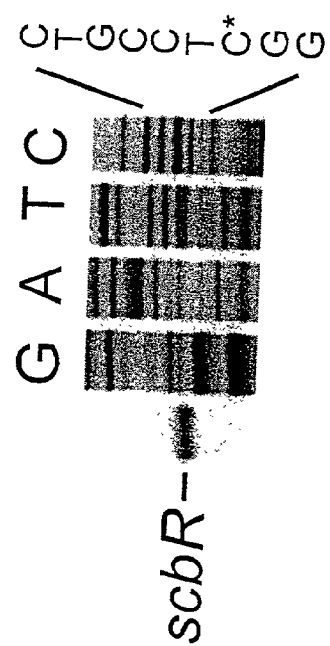
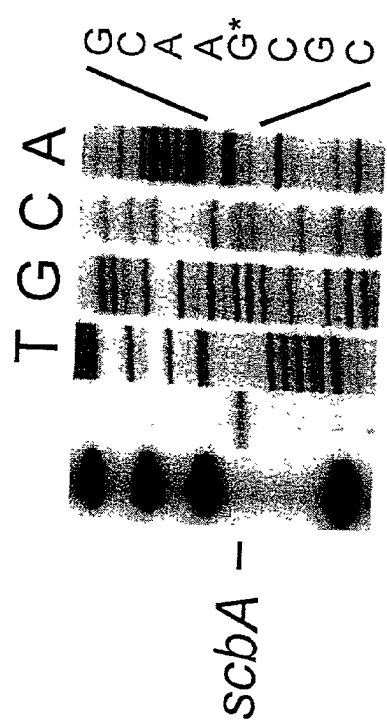

Fig. 4A
PCR fragment    9*+10        9+10*
*labelled oligo
JM101/scbR
crude extract    − +         − +
protein
concentration (μl)   A G         G A   2.5 1.25 0.16
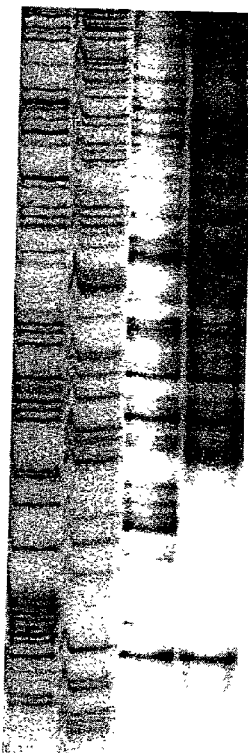
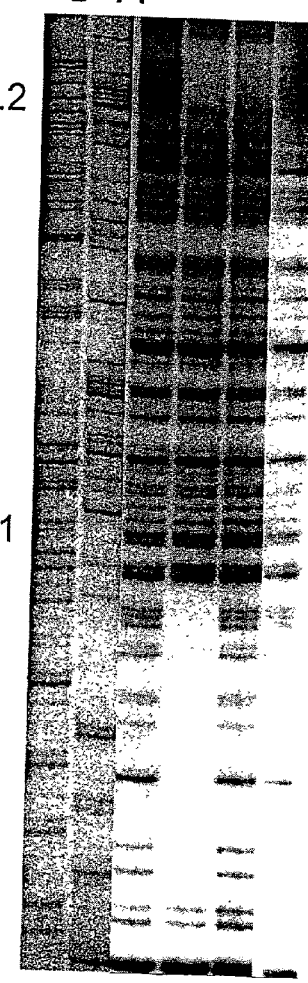
No.2
No.1
No.1
No.2

Fig. 4B

```
     GGGCAGGACGGCGGTGACCGAGAACCGGTCACCGCCCTTCGGTATCCAGCTGACCGGGAA
  1  ---------+---------+---------+---------+---------+---------+  60
     CCCGTCCTGCCGCCACTGGCTCTTGGCCAGTGGCGGGAAGCCATAGGTCGACTGGCCCTT
       P  L  V  A  T  V  S  F  R  D  G  G  K  P  I  W  S  V  P  F
                                             -67   binding site No.2

CGCGTCCTGCACCCTGGTCCGGTGGACAAGCGCCATCGGAACCGGCAATGCGGTTTGTTC
 61  ---------+---------+---------+---------+---------+---------+ 120
     GCGCAGGACGTGGGACCAGGCCACCTGTTCGCGGTAGCCTTGGCCGTTACGCCAAACAAG
       A  D  Q  V  R  T  R  H  V  L  A  M  P  V  P  L  A  T  Q  E
       -41                                  +1    pscbR
     GATCGAGTTGGCATCGGACGCAGAATTGATCAAAACTACTGCTTCGGGCATGGGTCCCCC
121  ---------+---------+---------+---------+---------+---------+ 180
     CTAGCTCAACCGTAGCCTGCGTCTTAACTAGTTTTGATGACGAAGCCCGTACCCAGGGGG
       I  S  N  A  D  S  A  S  N  I  L  V  V  A  E  P  M [ScbA]

CCAGGAATCATGTGATGCCGAGCTGTTCTGTATGCGCGAACGTTAAGATACAGACTGAGC
181  ---------+---------+---------+---------+---------+---------+ 240
     GGTCCTTAGTACACTACGGCTCGACAAGACATACGCGCTTGCAATTCTATGTCTGACTCG
                              pscbA   +1   -4   binding site No.1

GGTTTTTTTTCTATCCTTCCCGGGGGAGACATGAACAAGGAGGCAGGCATGGCCAAGCAG
241  ---------+---------+---------+---------+---------+---------+ 300
     CCAAAAAAAAGATAGGAAGGGCCCCCTCTGTACTTGTTCCTCCGTCCGTACCGGTTCGTC
             -33                                    [ScbR] M  A  K  Q

GACCGGGCGATCCGCACGCGGCAGACGATCCTGGACGCCGCGGCGCAGGTCTTCGAGAAG
301  ---------+---------+---------+---------+---------+---------+ 360
     CTGGCCCGCTAGGCGTGCGCCGTCTGCTAGGACCTGCGGCGCCGCGTCCAGAAGCTCTTC
       D  R  A  I  R  T  R  Q  T  I  L  D  A  A  A  Q  V  F  E  K

CAGGGCTACCAAGCTGCCACGATCACGGAGATCCTCAAGGT
361  ---------+---------+---------+---------+- 401
     GTCCCGATGGTTCGACGGTGCTAGTGCCTCTAGGAGTTCCA
       Q  G  Y  Q  A  A  T  I  T  E  I  L  K
```

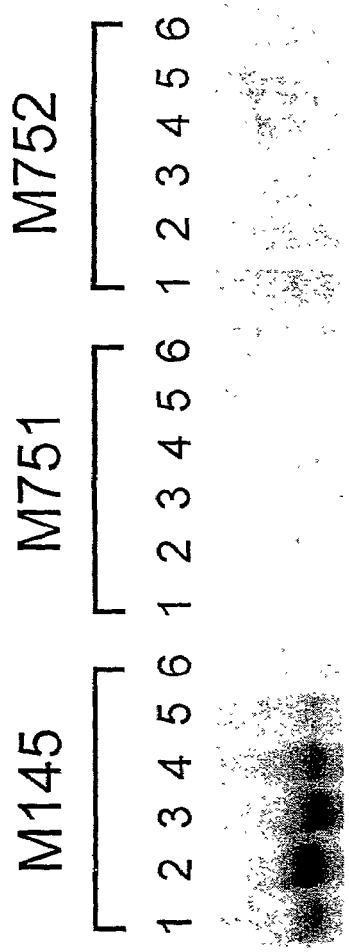
Fig. 7A

Fig. 8

SCB1 concentration    0 ng    31.25 ng scbA scbR hrdB

Fig. 9: ScbR amino acid sequence

MAKQDRAIRTRQTILDAAAQVFEKQGYQAATITEILKVAGVTKG
ALYFHFQSKEELALGVFDAQEPPQAVPEQPLRLQELIDMGMLFCHRLRTNVVARAGVR
LSMDQQAHGLDRRGPFRRWHETLLKLLNQAKENGELLPHVVTTDSADLYVGTFAGIQV
VSQTVSDYQDLEHRYALLQKHILPAIAVPSVLAALDLSEERGARLAAELAPTGKD

Fig. 10: ScbA amino acid sequence

MPEAVVLINSASDANSIEQTALPVPMALVHRTRVQDAFPVSWIP
KGGDRFSVTAVLPHDHPFFAPVHGDRHDPLLIAETLRQAAMLVFHAGYGVPVGYHFLM
TLDYTCHLDHLGVSGEVAELEVEVACSQLKFRGGQPVQGQVDWAVRRAGRLAATGTA
TTRFTSPQVYRRMRGDFATPTASVPGTAPVPAARAGRTRDEDVVLSASSQQDTWRLRV
DTSHPTLFQRPNDHVPGMLLLEAARQAACLVTGPAPFVPSIGGTRFVRYAEFDSPCWI
QATVRPGPAAGLTTVRVTGHQDGSLVFLTTLSGPAFSG

Fig. 11: ScbB amino acid sequence

MRAHGTRYGRPLEGKTALVTGGSRGIGRGIALRLAADGALVAVH
YGSSEAAARETVETIRSSGGQALAIRAELGVVGDAAALYAAFDAGMGEFGVPPEFDIL
VNNAGVSGSGRITEVTEEVFDRLVAVNVRAPLFLVQHGLKRLRDGGRIINISSAATRR
AFPESIGYAMTKGAVDTLTLALARQLGERGITVNAVAPGFVETDMNARRRQTPEAAAA
LAAYSVFNRIGRPDDIADVVAFLASDDSRWITGQYVDATGGTIL

Fig. 14

DNA_SEQUENCE  Length: 4346kb..

```
   1  GTCGACGACG GCGTCGGGTT CGACGCCGAC GCGGTACTCG TTCCCGGCCA
      HincII
  51  CCGGGCACCG GGTCTGCGCT CGATGACCGA CCGCATCGAG GACGTCGGCT
 101  GGCGGCTCCT GATAGTGAGC GGCCCCGCCG GCGGCACGCA CATCGACGTC
 151  CATCTCCCAC TGCGCCCCCG GAAAGTGAGC ACCGCACCGC GGACGTGACG
 201  CCATGGGAGG GCCACGTCCG CGGACGGATC ACCCCTGGCT TCGGCCGAAG
 251  GCTTCCGCGT GGTCCGCCGC CCAGATGCGG AACGGCCTGG CGGGCCGGCC
 301  CGTCACTTCC CGCACGGTCG GCACGACCTG CGCCTTGGCC CCCGCCCGCT
 351  GCCGCTCGGC GCTCTCCAGG AACGCGTCGG CGACGGGCCT CGGATACTTC
 401  CGGAGCATCT GCTCGCGCGC CGCCTCCAGC CCCAGCTCCT CGAAACGCAG
 451  TGACCGCCCC AGCACCTCGG AGAGCCGCGC CGTCTGCTGC CTGGCGGTGA
 501  TCGCCTCGGG CCCGGACAGC GCGTACGCCC GTCCCTCGTG GCCGGGCCGG
 551  GTCAGTGCCC TGACCGCCAC TTCCGCGATG TCGCGCGGAT CGACGCAGGC
 601  AACCGGGGAC GTGCCGTACA GCGCGCGGAC CACGCCGTCG ACCGGATGG
 651  CGGGCGCCCA GGACAGCGTG TTGGACATGA AGGTCCTGGC CCGCAGGAAG
 701  GTCCAGTCTA GCCCGGACTC GCGTACGGCC CGCTCGTTCT CGCGCTGCCG
 751  CCGCGTGATG AAGTCGTCCG CGCCCGGTTC CCCCACCGCG AGCATGGACA
 801  GCTTCACCAG GTGCCGGACG CCGGCCTCGC GCGCCGCCGC CGCGAAACGC
 851  TCGTCGTCCG GCTCGGTGGC ACTGTTCGTG ACGAGGAACG CCGCCCGCAC
 901  CCCGTTGAGG GCCCGGTCCA GGCCCGGGCG GTCGGCGTAC TCGCCCGCGC
 951  AGACCTCGAC GTTCGGGCCG GTGACGGTCA CCCGTTCCGG CCGCCGGGCG
1001  AGGACTCTGA CGGGACCGGT CCGGGCCAGC AGGTGGGCGA CCTGACGGCC
1051  GACCACACCG GTCACGCCGG TCACAAGAAT CACTCGGGGC TCCTCTCGGG
1101  CAGCGAGGCA GGGGCGCCTC CGaacAtACA TATGAGGGGA Agggcaggat
1151  ctgccccggg gcgcgaaccg gcgatgttcg cgccccGGGG CCGGTGCTTC
1201  AGCCGGAGAA CGCGGGGCCG GACAGCGTGG TGAGGAAGAC GAGGCTGCCG
1251  TCCTGATGCC CGGTGACCCG CACGGTGGTC AGCCCCGCCG CCGGCCCCGG
1301  CCGGACCGTC GCCTGGATC/C AGCACGGGCT GTCGAACTCC GCGTACCGGA
                   BamHI
```

1351 CGAACCGGGT GCCGCCGATC GACGGCACGA AGGGCGCCGG ACCGGTCACG
1401 AGGCACGCCG CCTGCCGTGC CGCCTCGAGC AGCAGCATGC CCGGTACGTG
1451 GTCGTTGGGG CGCTGGAAGA GGGTCGGGTG ACTGGTGTCC ACCCGCAGTC
1501 GCCACGTGTC CTGCTGCGAA CTCGCCGACA GGACCACGTC CTCGTCGCGG
1551 GTGCGACCGG CGCGCGCCGC GGGCACGGGC GCGGTCCCGG CACCGATGC
1601 GGTGGGAGTC GCGAAGTCGC CGCGCATCCG CCGGTAGACT TGAGGACTGG
1651 TGAAGCGCGT CGTGGCAGTC CCCGTGGCAG CGAGCCGTCC GGCGCGGCGC
1701 ACGGCCCAGT CCACCTGTCC CTGTACGGGC TGCCCGCCGC GGAACTTCAG
1751 CTGGGAACAG GCCACTTCCA CCTCCAGCTC CGCGACCTCG CCCGACACGC
1801 CGAGGTGGTC GAGGTGGCAG GTGTAGTCCA GCGTGGCCAT CAGGAAGTGG
1851 TAGCCCACCG GCACGCCGTA GCCGGCGTGG AAGACGAGCA TCGCCGCCTG
1901 ACGCAGGGTC TCGGCGATCA GCAGCGGATC GTGTCGGTCC CCGTGGACCG
1951 GTGCGAAGAA CGGGTGGTCG TGGGGCAGGA CGGCGGTGAC CGAGAACCGG
2001 TCACCGCCCT TCGGTATCCA G/CTGACCGGG AACGCGTCCT GCACCCTGGT
                             *PvuII*
2051 CCGGTGGACA AGCGCCATCG GAACCGGCAA TGCGGTTTGT TCGATCGAGT
2101 TGGCATCGGA CGCAGAATTG ATCAAAACTA CTGCTTCGGG CATGGGTCCC
2151 CCCCAGGAAT CATGTGATGC CGAGCTGTTC TGTATGCGCG AACGTTAAGA
2201 TACAGACTGA GCGGTTTTTT TTCTATCCTT CCCGGGGGAG ACATGAACAA
2251 GGAGGCAGGC ATGGCCAAGC AGGACCGGGC GATCCGCACG CGGCAGACGA
2301 TCCTGGACGC CGCGGCGCAG GTCTTCGAGA AGCAGGGCTA CCAAGCTGCC
2351 ACGATCACG/G AGATCCTCAA GGTGGCCGGG GTGACCAAGG GAGCCCTCTA
                CTGCA/GATG designed primer to generate *PstI* site
                *PstI*
2401 CTTCCACTTC CAGTCCAAGG AAGAACTGGC GCTGGGCGTC TTCGACGCCC
2451 AGGAACCACC ACAGGCCGTT CCGGAGCAAC CCCTCCGGCT GCAAGAACTC
2501 ATCGACATGG GCATGTTGTT CTGTCACCGC TTGCGCACGA ACGTCGTGGC
2551 CCGGGCCGGC GTGCGCCTCT CCATGGACCA GCAGGCGCAC GGTCTCGATC
2601 GCCGAGGACC CTTCCGTCGC TGGCACGAGA CACTCCTGAA GCTGCTGAAC
2651 CAGGCCAAGG AGAACGGTGA GTTGCTGCCC CATGTGGTCA CCACCGACTC
2701 GGCCGATCTC TACGTGGGCA CGTTCGCCGG GATACAGGTC GTGTCCCAGA
2751 CGGTCAGCGA CTACCAGGAC CTCGAACACC GCTACGCGCT GCTGCA/GAAG
                                                      *PstI*

```
2801  CACATCCTGC  CCGCCATCGC  GGTTCCCTCC  GTGCTGGCCG  CGCTCGATCT
2851  CTCCGAGGAG  CGCGGAGCAC  GCCTCGCGGC  CGAACTGGCA  CCGACCGGGA
2901  AGGACTGACC  GCCGAAGCGC  CCGCACCGGA  TACCGACCCG  CCGTGCCCGA
2951  GCGGCCGACC  GGGGCCGCCT  ACGGGCCCGG  CGGCGGGCCC  GTAGGTCTGC
3001  CCTGCGTACC  GAAGCGTGGC  GGGTCAGAGA  ATCGTTCCGC  CTGTGGCATC
3051  GACGTACTGG  CCGGTGATCC  ACCGTGAGTC  GTCGGAGGCC  AGAAAGGCCA
3101  CCACGTCGGC  GATGTCGTCG  GGTCTGCCGA  TGCGGTTGAA  CACGGAGTTG
3151  GCGGCCAGTG  CCGCGGCCGC  CTCGGGGGTC  TGCCGCCGCC  GTGCGTTCAT
3201  GTCCGTCTCC  ACGAAACCCG  GCGCCACCGC  GTTGACCGTG  ATCCCCCGTT
3251  CCCCCAGTTG  CCTGGCCAGG  GCGAGCGTGA  GCGTGTCCAC  CGCACCCTTG
3301  GTCATCGCGT  ATCCGATGGA  CTCGGGGAAC  GCGCGCCGGG  TCGCGGCAGA
3351  CGAGATGTTG  ATGATCCGCC  CGCCGTCGCG  CAGTCGTTTC  AGTCCGTGCT
3401  GGACCAGGAA  CAGCGGTGCC  CGGACGTTGA  CGGCGACCAG  TCGGTCGAAG
                                        *HincII*
3451  ACCTCCTCGG  TGACTTCCGT  GATCCGTCCC  GAGCCGCTGA  CGCCCGCGTT
3501  GTTCACCAGG  ATGTCGAACT  CGGGCGGCAC  TCCGAACTCG  CCCATCCCGG
3551  CGTCGAACGC  CGCGTAGAGC  GCGGCCGCGT  CACCCACGAC  GCCGAGTTCG
3601  GCCCGGATGG  CCAACGCCTG  TCCGCCGCTG  CTCCGGATGG  TCTCGACGGT
3651  CTCTCGCGCC  GCCGCCTCGC  TGCTGCCGTA  GTGGACTGCC  ACGAGCGCCC
3701  CGTCCGCGGC  CAGCCGCAGG  GCGATACCGC  GTCCGATGCC  CCGGCTTCCC
3751  CCGGTCACCA  GGGCGGTCTT  GCCCTCCAGC  GGTCTTCCAT  ACCTCGTCCC
3801  ATGTGCACGC  ATATCAGCCC  CCGCCGTGCG  TGAGCGACCC  ATGGCGGCCG
3851  CTCGGCCGTT  CGAATCGACG  GTCACAGCCT  ACCTGTGACC  GCGTCAGACG
3901  GGGCCGGAGT  GGCCCGGTTG  GACGGCTGGG  GCCAGATCGG  GCGGCGCGCA
3951  CGGGGAACCG  GCGCCGGTCA  GGGGTCAGGG  GTCGCCGGGA  CCGCCCAGGC
4001  CGGTCAGGGC  ACCGACCGGA  TCGAGGTCGG  GCGTGCCACG  CGGCCACCAG
4051  TCCTCGCGGC  CCAGCTCCGA  CTCGTACGCG  TACCAGAGCC  CGGTCCGGCC
4101  GAGTCTGAGC  TGGACGTGGC  CGCGCGGGTG  GGTGAGGCGG  TTGCGCCAGG
4151  GGCGGAAGGC  GGGGAGGTCG  GCGGCGAGCA  TCATGGGGCG  GGCGCGGTCG
4201  AAACGGCCGG  CCGGCGGGTC  CCAGGGCTCC  TCCAGGACGT  CTAGACCCGC
4251  CAACCCGCCC  TGCCGCCAGG  CGGCGACGGC  CCGCGCCAGC  TCCGCCGTGT
4301  CGCGTCCGGC  GGCCGAGGCG  AGCGACGCGT  AGAGCGCGCG  GGTACC
                                                        *KpnI*
```

METHODS OF INCREASING ANTIBIOTIC PRODUCTION IN *STREPTOMYCES* BY DELETION OF THE SCBA GENE

REFERENCE TO PROVISIONAL APPLICATION

This application claims the benefit of U.S. Provisional Application No. 60/242,561 filed on Oct. 23, 2000, the entire disclosure of which is incorporated by reference herein.

FIELD OF THE INVENTION

The present invention relates to methods and materials for controlling antibiotic production in species of *Streptomyces*, especially increasing antibiotic production in *Streptomyces coelicolor* and *S. lividans*.

INTRODUCTION

In addition to undergoing a complex process of morphological differentiation, streptomycetes are renowned for their ability to produce a vast array of secondary metabolites, many of which possess antibiotic or other pharmacologically useful activities. Most of these secondary metabolites are the products of complex biosynthetic pathways that are activated in a growth phase-dependent manner. While the production of antibiotics in liquid culture is generally limited to stationary phase, in surface-grown cultures it usually coincides with the onset of morphological differentiation (Chater and Bibb, 1997).

In several streptomycetes, γ-butyrolactones (GBLs) have been shown to play important, if not crucial, roles in determining the onset of antibiotic production and morphological differentiation (Horinouchi and Beppu, 1994; Yamada, 1999). The most characterised γ-butyrolactone is A-factor (2-isocaryloyl-3R-hydroxymethyl-γ-butyrolactone), which is required for both streptomycin production and sporulation in *Streptomyces griseus* (Mori, 1983; Horinouchi and Beppu, 1994). Other well-studied γ-butyrolactones include virginiae butanolides (VB), which appears to control virginiamycin production in *Streptomyces virginiae* (Yamada et al., 1987; Kondo et al., 1989), and IM-2, which elicits the production of showdomycin and minimycin in *Streptomyces lavendulae* FRI-5 (Sato et al., 1989).

Although the details of A-factor synthesis have not been elucidated, a putative A-factor biosynthetic gene, afsA, was cloned from *S. griseus* and sequenced. Its predicted translation product does not resemble any protein of known function (Horinouchi et al., 1989). afsA mutants of *S. griseus* are deficient in A-factor synthesis, and hence in streptomycin production and sporulation. Moreover, cloning of afsA in multiple copies leads to precocious streptomycin production in *S. griseus*, and to the production of a compound with A-factor activity in other streptomycetes that normally do not make it (Horinouchi et al, 1985). Culture supernatants of an *Escherichia coli* strain over-expressing afsA restored streptomycin production and sporulation in an A-factor-deficient mutant of *S. griseus* (Ando et al., 1997).

A-factor is detected in culture supernatants of *S. griseus* just before the onset of streptomycin production. It diffuses freely across the cytoplasmic membrane, and binds with high affinity to a cytoplasmic A-factor-binding protein, ArpA (Onaka et al, 1995). In the absence of A-factor, ArpA acts as a negative regulator of both streptomycin production and sporulation by repressing transcription of the pleiotropic regulatory gene adpA (Ohnishi et al., 1999). Homologues of afsA and/or arpA have been isolated from several streptomycetes, including *S. virginiae* (Okamoto et al., 1995; Kinoshita et al., 1997), *S. lavendulae* (Waki et al., 1997), *S. coelicolor* (Onaka et al., 1998) and *S. fradiae* (Fouces et al., 1999; Bate et al., 1999).

*S. coelicolor* is the most genetically characterised streptomycete. It produces at least four chemically distinct antibiotics. Two of these, actinorhodin (Act) and undecylprodigiosin (Red), are pigmented. The stationary phase production of Act and Red results from transcriptional activation of the pathway-specific activator genes actII-ORF4 and redD, respectively (Gramajo et al., 1993; Takano et al., 1992). Moreover, production of Act and Red in exponential phase appears to be prevented only by the absence of a threshold concentration of the pathway specific activator proteins.

Recently, four extracellular compounds were identified in culture supernatants of *Streptomyces coelicolor* A3(2) that elicited the precocious production of the antibiotics actinorhodin (Act) and undecylprodigiosin (Red) when added to the producing strain; none of the compounds induced morphological differentiation. One of these stimulatory factors, SCB1, was purified to homogeneity and shown by structural elucidation to be a γ-butyrolactone (Takano et al., 2000).

SUMMARY OF THE INVENTION AND DETAILED DESCRIPTION

The present inventors have identified genes of *S. coelicolor* which are involved in the regulation of Act and Red production. One gene, scbA, is a homologue of afsA (A-factor synthetase of *S. griseus*), and the other, scbR, encodes a γ-butyrolactone binding protein. By analogy with the *S. griseus* system, ScbR was expected to be a repressor of the pathway-specific activator genes actII-ORF4 and redD. Release of such repression upon binding of ScbR by the GBL SCB1 at high cell densities would lead to antibiotic expression.

However, it was found that ScbR binds to the transcription start sites of scbA and scbR, and is released by addition of SCB1 from *S. coelicolor*. An in-frame deletion mutant of scbA (a gene involved in GBL synthesis) shows overproduction of Act and Red (when lack of antibiotic production might have been expected) and an in-frame deletion mutant of scbR shows delay in Red production and earlier Act production (scbR—see FIG. 5A). These phenotypes therefore differ from what might be expected by analogy to the *S. griseus* A-factor system.

Moreover, the inventors have found that *S. lividans* strains carrying the same in-frame deletion mutant of scbA, in place of the wild-type scbA gene usually present in *S. lividans*, also overproduce Act and Red.

The inventors propose, therefore, that mutations to homolgues of scbA and scbR in other *Streptomyces* species may have similar effects.

Accordingly, in a first aspect, the present invention provides a method of modifying an antibiotic-producing strain of a *Streptomyces* species to increase antibiotic production in said strain, the method comprising functionally deleting in said strain a gene which is the scbA gene of *Streptomyces coelicolor* or a homologue thereof.

In a second aspect, the present invention provides a method of modifying an antibiotic-producing strain of a *Streptomyces* species to alter the timing of antibiotic production in said strain, the method comprising functionally deleting in said strain a gene which is the scbR gene of *Streptomyces coelicolor* or a homologue thereof.

While it is appreciated that these effects will not be found in relation at least to streptomycin production in *S. griseus*, and perhaps in some other *Streptomyces* species, it is thought that the effects may not be confined to the exemplified species of *S. coelicolor* and *S. lividans*. It will be possible for the skilled person to repeat the experimental disclosure presented herein on other *Streptomyces* species, thereby to identify other species in which similar effects occur. In particular, it will be possible to identify in other species of *Streptomyces* genes which are homologues of scbR and scbA in an analogous way to the identification herein of scbR and scbA. Following identification of the genes, it will be possible to create strains in which these genes are functionally deleted, and to compare the extent and/or timing of antibiotic production in those modified strains with the extent and/or timing of production in the parent strain. Those modified strains in which similar effects are found to those presented herein are regarded also to be part of the invention.

Accordingly, in a third aspect, the present invention provides a modified strain of a *Streptomyces* species, the modified strain having a functional deletion of a gene which is the scbA gene of *S. coelicolor* or a homologue thereof, whereby production of at least one antibiotic in said modified strain is increased compared to a wild-type strain of said *Streptomyces* species.

Similarly, in a fourth aspect, the present invention provides a modified strain of a *Streptomyces* species, the modified strain having a functional deletion of a gene which is the scbR gene of *S. coelicolor* or a homologue thereof, whereby the timing of production of at least one antibiotic in said modified strain is altered compared to a wild-type strain of said *Streptomyces* species.

In a fifth aspect, the present invention provides a method of producing an antibiotic, the method comprising providing a modified *Streptomyces* strain of any preceding aspect, and culturing said strain under conditions suitable for production of antibiotic.

The method may also comprise the additional step of purifying the antibiotic from the culture medium. It may also comprise the further step of formulating the antibiotic as a pharmaceutical.

The scbR and scbA genes are believed to be new, as is a further gene, designated scbB, which is downstream of scbR and which shows homology to the C-5 ketoreductase gene of *S. avermitilis*. scbB is predicted to modify the C-6 of SCB1 from keto to hydroxyl, and may therefore be important in providing specificity of SCB1 as the cognate GBL of scbR.

In a sixth aspect, the present invention provides a nucleic acid comprising a nucleotide sequence having at least about 80% identity with a nucleic acid sequence selected from the group consisting of (1) nucleotides 3032 to 3679, (2) nucleotides 2914 to 1970, and (3) nucleotides 4529 to 3795, reading 5' to 3', of the nucleic acid deposited as EMBL AJ007731, which may alternatively be defined as (1) nucleotides 2261–2908, (2) nucleotides 2142–1199 and (3) nucleotides 3758–3024, respectively of FIG. 14.

As will be evident from FIG. 1, both strands of DNA in this region encode polypeptides. Nucleotide numbering is given in relation to the strand which runs from 5' to 3' from right to left in FIG. 1. The sequence of part of this strand is given in FIG. 14. However, the coding sequences of scbA and scbB are on the complementary strand. References to the nucleotide sequences in EMBL AJ007731 and FIG. 14 which relate to these genes (i.e. where the nucleotide numbering is shown as [higher number]-[lower number]) should therefore be interpreted as references to the strand complementary to that shown.

Preferably the nucleic acid sequence identity is at least 85%, 90%, 95%, 98% or 99% or is 100%.

In a seventh aspect, the present invention provides a nucleic acid comprising a nucleotide sequence which encodes a polypeptide having at least about 70% amino acid sequence identity with an amino acid sequence selected from the group consisting of (1) the amino acid sequence of ScbR, as shown in FIG. 9 (SEQ ID NO: 16), (2) the amino acid sequence of ScbA, as shown in FIG. 10 (SEQ ID NO: 17), and (3) the amino acid sequence of ScbB, as shown in FIG. 11 (SEQ ID NO: 18).

In further aspects, the present invention provides: polypeptides encoded by the nucleic acid molecules of the sixth and seventh aspects; vectors including the nucleic acids of those aspects, optionally in operative association with control sequences, e.g. promoter and/or enhancer sequences; host cells transfected with said vectors; and methods of producing said polypeptides, comprising culturing said host cells under conditions suitable for polypeptide production and extracting said polypeptides from the culture medium.

In a still further aspect, the present invention provides a method for identifying *Streptomyces* species in which antibiotic production is increased by functionally deleting the scbA gene of *S. coelicolor* or a homologue thereof, the method comprising functionally deleting in an antibiotic-producing strain of a *Streptomyces* species the scbA gene of *S. coelicolor* or a homologue thereof, culturing said strain under conditions suitable for the production of antibiotic, and determining whether antibiotic production in said strain is increased.

Similarly, the invention also provides a method for identifying *Streptomyces* species in which the timing of antibiotic production is altered by functionally deleting the scbR gene of *S. coelicolor* or a homologue thereof, the method comprising functionally deleting in an antibiotic-producing strain of a *Streptomyces* species the scbR gene of *S. coelicolor* or a homologue thereof, culturing said strain under conditions suitable for the production of antibiotic, and determining whether the timing of antibiotic production in said strain is altered.

In a further aspect, the invention provides a method for producing an antibiotic, the method comprising, following identification of a *Streptomyces* species according to the preceding aspect, providing a strain of said species having a functional deletion of said scbA or scbR gene of *S. coelicolor* or homologue thereof, and culturing said strain under conditions suitable for antibiotic production.

As before, the method may further comprise the step of purifying the antibiotic from the culture medium. It may also comprise the step of formulating the antibiotic as a pharmaceutical.

As used herein, the term "functional deletion" of a gene may mean any alteration of the nucleic acid in a cell or cells of the strain containing the functional deletion, which alteration has the effect of preventing normal expression of that gene. For example, the gene may comprise a deletion in the coding sequence, leading to a shortened transcript which is translated into a protein lacking the normal function of the expression product of the gene; or the transcriptional and/or translational regulatory sites (e.g. promoter and/or enhancer sequences) may be altered to prevent normal transcription and/or translation of the gene; or the coding sequence may contain an insertion or mutation (e.g. to introduce or produce a stop codon or to cause a shift in reading frame), leading to a non-functional expression product. Alterations of the coding sequence may be in frame or may cause a shift in reading frame. As a further alternative, the cell(s) may be modified to produce antisense mRNA, which prevents correct translation, preventing gene expression even if the gene itself is unmodified.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS USA* 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U.S. Pat. No. 5,231,020.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene. Total complementarity or similarity of sequence is not essential. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene.

Preferred *Streptomyces* species for the practice of the invention are species which possess adjacent and divergent scbA and scbR genes of *S. coelicolor* or adjacent and divergent homologues thereof, since it is thought that this arrangement of genes may correlate with the effects on amount and timing of antibiotic production seen in *S. coelicolor* and *S. lividans*.

The closely related species *S. coelicolor*, *S. violaceoruber*, *S. lividans* and *S. parvulus* are particularly preferred. Strains of such species (i.e. wild-type strains) are commonly available, e.g. from the ATCC, for example under ATCC deposit numbers 12434 for *S. parvulus* and 19832 for *S. violaceoruber*. *S. coelicolor* A3(2) and *S. lividans* 66 are particularly preferred wild-type strains and are available from the John Innes Culture Collection (Norwich, UK) under JICC deposit numbers 1147 and 1326, respectively. However, the invention is not limited to such particular strains.

The present invention may exclude the modification of barX and/or farX, the afsA homologues in *S. virginiae* and *S. fradiae*, respectively.

A gene of a *Streptomyces* species or strain, which gene is a "homologue" of or is "homologous" to the scbA gene of *S. coelicolor*, may be the gene which shows greatest deduced amino acid sequence identity to scbA of all genes of said species or strain; alternatively or additionally, it may be a gene which is capable of specific hybridisation with the amplification product obtained using the primers oligo1 (5'-GACCACGT(CG)CC(CG)GGCATG; SEQ ID NO: 1) and oligo2 (5'-GTCCTG(CG)TGGCC(CG)GT(CG)AC(CG)CG(CG)AC; (SEQ ID NO: 2) to amplify total DNA of said species or strain (bracketed nucleotides indicate positions of degeneracy); alternatively or additionally, it may be a gene encoding a polypeptide having at least about 35% sequence identity with the deduced amino acid sequence of scbA as shown in FIG. 10, preferably at least about 40% (which is the homology found between scbA and other homologues of the afsA gene of *S. griseus*) more preferably about 50%, 60%, 65% (which is the homology found between scbA and afsA of *S. griseus*), 70%, 80%, 90%, or 95%.

A gene of a *Streptomyces* species or strain, which gene is a "homologue" of or is "homologous" to the scbR gene of *S. coelicolor*, may be the gene which shows greatest deduced amino acid sequence identity to scbR of all genes of said species or strain; alternatively or additionally, it may be a gene which is adjacent to and divergent from a gene which is capable of specific hybridisation with the amplification product obtained using the primers oligo1 (5'-GACCACGT(CG)CC(CG)GGCATG (SEQ ID NO: 1) and oligo2 (5'-GTCCTG(CG)TGGCC(CG)GT(CG)AC(CG)CG(CG) AC; (SEQ ID NO: 2) to amplify total DNA of said species or strain (bracketed nucleotides indicate positions of degeneracy); alternatively or additionally, it may be a gene encoding a polypeptide having at least about 35% sequence identity with the deduced amino acid sequence of scbR as shown in FIG. 9, preferably at least about 40%, more preferably about 45% (which is the homology found between scbR and arpA of *S. griseus*), 50%, 55% (which is the homology found between scbR and the FarA gene of *S. lavendulae*) 60%, 65%, 70%, 80%, 90%, or 95%.

"Percent (%) amino acid sequence identity" is defined as the percentage of amino acid residues in a candidate sequence that are identical with the amino acid residues in the sequence with which it is being compared, after aligning the sequences and introducing gaps, if necessary, to achieve the maximum percent sequence identify, and not considering any conservative substitution as part of the sequence identity. The % identity values used herein are generated by WU-BLAST-2 which was obtained from Altschul et al. WU-BLAST-2 uses several search parameters, most of which are set to the default values. The adjustable parameters are set with the following values: overlap span=1, overlap fraction=0.125, word threshold (T)=11. The HSPS and HSPS2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by te total number of residues of the "longer" sequence in the aligned region, multiplied by 100. The 'longer" sequence is the one having the most actual residues in the aligned region (gaps introduced by WU-BLAST-2 to maximize the alignment score are ignored).

"Percent (%) nucleic acid sequence identity" is defined as the percentage of nucleotide residues in a candidate sequence that are identical with the nucleotide residues in the sequence under comparison. The identity values used herein were generated by the BLASTN module of WU BLAST-2 set to the default parameters, with overlap span and overlap fraction set to 1 and 0.125, respectively.

Methods of genetically manipulating *Streptomyces*, culturing *Streptomyces* under conditions suitable for antibiotic production and purifying antibiotics from Streptomycete cell culture medium are well known to the skilled person, e.g. from Hopwood et al. (1985) and Kieser et al (2000).

Similarly, methods of formulating antibiotics as pharmaceuticals are well known in the art. Such pharmaceutical formulations may comprise, in addition to the antibiotic, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, transdermal, transmucosal, intramuscular, intraperitoneal routes.

Suitable carriers, adjuvants, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 2nd edition, 1994.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the antiobiotic will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations suitable for transmucosal administration include liquids, solutions, suspensions, emulsions, suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Ointments are typically prepared from the active compound and a paraffinic or a water-miscible ointment base.

Creams are typically prepared from the antibiotic and an oil-in-water cream base. The aqueous phase of the cream base may include at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences (supra).

A pharmaceutical formulation may be administered alone or in combination with other treatments, either simultaneously or sequentially dependent upon the condition to be treated.

BRIEF DESCRIPTION OF THE FIGURES

FIG. 2a S1 nuclease mapping of the transcriptional start site of scbA and scbR. Asterisks indicate the probable start points of the transcription; the sequences given are those of the template strand. Lanes T, G, C, and A are sequence ladders derived from the same primers as the probe generated by PCR and using the Taqtrack kit along with the these primers.

FIG. 4a Dnase I footprinting experiment of ScbR. Protection of the scbA and scbR promoter region by ScbR from cleavage by Dnase I is shown by vertical lines. No.1 denotes ScbR binding site No.1 and No.2 binding site No.2. Both DNA strands were tested for protection by Dnase I by using two different $^{32}P$ labelled oligonucleotides. The A and G sequence ladder were used as size standards. Asterisk indicates the oligonucleotide which has been labelled. The presence or absence of crude extracts from E. coli JM101 harboring scbR is indicated by + or −. The numbers underneath the symbol > denote the concentration gradient of the crude extract added to the reaction.

FIG. 4b ScbR binding sites No.1 and No.2 from Dnase I footprinting experiments. The protected sequences are indicated by lines and the numbering is with respect to the transcriptional start site of scbA for binding site No.1 and scbR for binding site No.2. The arrows and pscbA, pscbR indicate the transcriptional start site and direction of scbA and scbR, respectively. [ScbA] (amino acid sequence is SEQ ID NO: 14) and [ScbR] (amino acid sequence is SEQ ID NO: 15) indicate the coding sequence for scbA and scbR, respectively. Nucleic acid sequences are SEQ ID NO: 12 (top) and SEQ ID NO: 13 (bottom).

FIG. 7a S1 nuclease mapping of scbA, scbR, and the major sigma factor hrdB, using RNA isolated from a liquid time course of S. coelicolor M145, M751 and M752 at the numbers indicated. The E, TRAN and S indicates the exponential, transition and stationary phases of growth, respectively, and the shaded box labelled RED and A denote the presence of undecylprodigiosin and actinorhodin in the mycelium. The numbers in the box denotes the measurement of antibiotic production, ACT for actinorhodin, and RED for undecylprodigiosin, respectively. Numbers in bold refer to the time points when the antibiotics were measured, which corresponds to the time of RNA isolation.

FIG. 7b Bioassay of supernatants isolated at the time of RNA isolation from M145. The numbers denotes the different time points indicated in FIG. 7a.

FIG. 8 S1 nuclease mapping of scbA, scbR, and the major sigma factor hrdB, using RNA isolated from M571 grown on liquid media SMM, with 0 or 31.25 ng final concentration addition of SCB1.

FIG. 9 Deduced amino acid sequence of ScbR (SEQ ID NO: 16).

FIG. 10 Deduced amino acid sequence of ScbA (SEQ ID NO: 17).

FIG. 11 Deduced amino acid sequence of ScbB (SEQ ID NO: 18).

FIG. 14 Nucleic acid sequence (SEQ ID NO: 19) of region containing scbA, scbR and scbB. M751 (ΔscbA) is deleted from nt position 1320 to 2021; M752 (ΔscbR) is deleted from nt position 2359 to 2796 with five bases added; pIJ6134 runs from nt position 2021 to 4346; and pIJ6140 runs from nt position 1 to 3430.

The work on which the present invention is based will now be described, by way of example only, with reference to these figures.

EXAMPLE 1 scbA—an S. coelicolor Homologue of afsA

Alignment of the amino acid sequences of AfsA from S. griseus and its homologue, BarX, from S. virginiae (Kinoshita et al., 1997), revealed two highly conserved regions (corresponding to amino acid residues 217–223 and 277–285 of AfsA). These sequences were used, with codon usage data derived from 64 Streptomyces genes (Wright and Bibb, 1992), to design degenerate oligonucleotides for use as primers in PCR. BamHI sites were incorporated at the 5′ end of each primer to allow subsequent cloning of the PCR product. An amplified fragment of the expected size (189 bp including the flanking BamHI sites) was obtained using S. coelicolor M145 DNA as template. The PCR product was cleaved with BamHI, and cloned in the BamHI site of the pUC19 derivative pIJ2925, yielding pIJ6114. Sequencing using universal and reverse primers revealed an afsA homologue of S. coelicolor, which was designated scbA.

Figure 1:
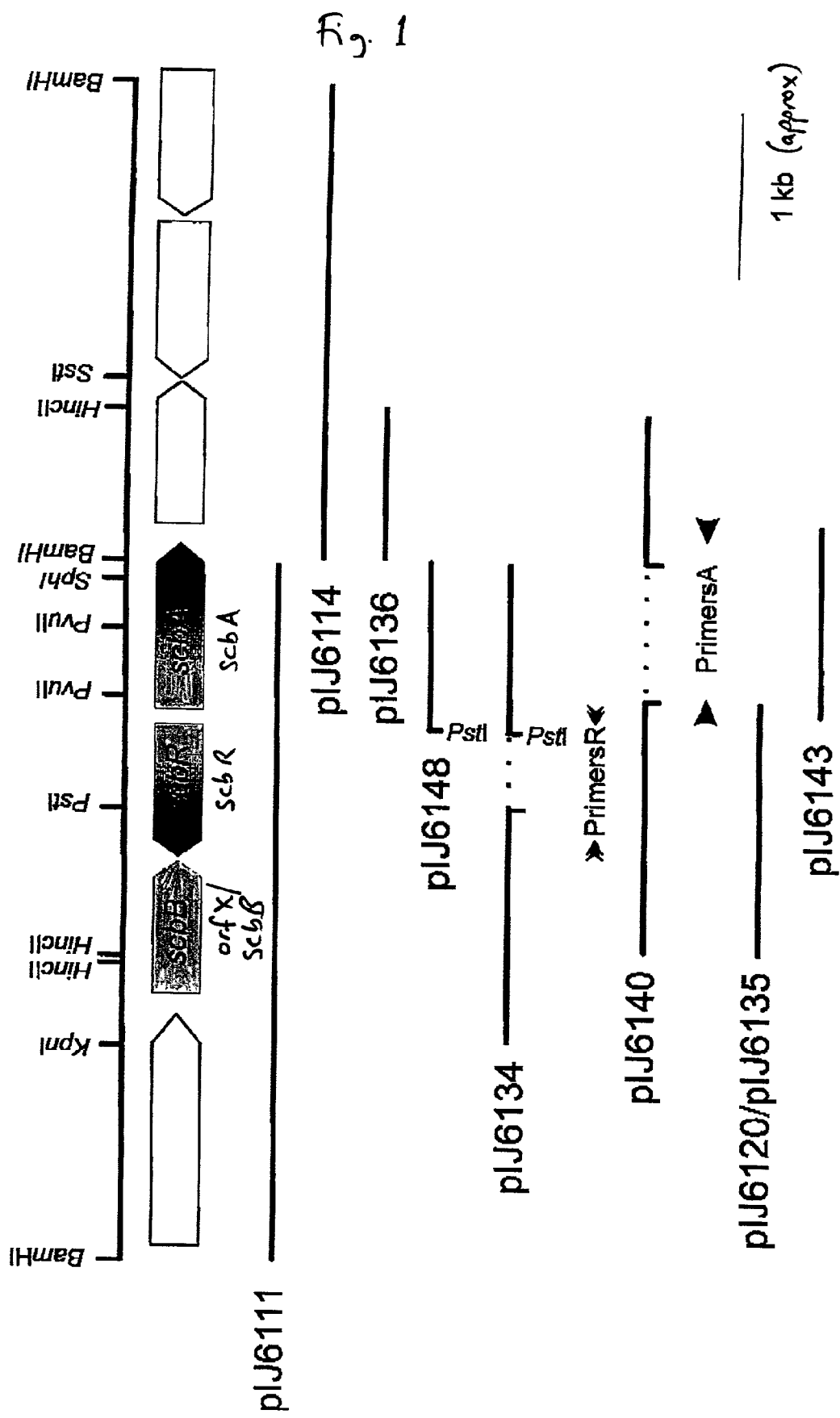
FIG. 1 Restriction map of 7.5 kb DNA fragment isolated from *S. coelicolor* which includes scbA and scbR. The positions of scbA, scbR, orfX (also referred to herein as scbB) are indicated by shaded boxes and the other ORFs with no apparent homology to other known *streptomyces* antibiotic regulatory genes (as assessed by the BLAST program) are indicated by open boxes. The ORFs are deduced from the FRAME program (Bibb et al., 1983). pIJ6111 and pIJ6114 were used for sequencing analysis of the 7.5 kb fragment. Restriction maps of the in-frame deletion mutant constructs are also shown. Dotted lines indicate the in-frame deletion of scbA for pIJ6120 or scbR for pIJ6124. The PstI site in pIJ6124 was generated by using a designed primer for PCR to allow ligation with the corresponding PstI site. The BamHI site in pIJ6140 was end filled and ligated with PvuII. Single arrows (PrimersR) and double arrows (PrimersA) denote the primers used to determine the scbR and scbA mutation, respectively, after the second crossover event. pIJ 6135 and pIJ6143 (insert cloned into pSET152) were used to complement the scbR and scbA mutant, respectively. pIJ6120 (insert in pIJ2925) was used to express ScbR for gel retardation and Dnase I footprinting experiments.

The BamHI insert of pIJ6110 was isolated and labelled with $^{32}P$ by random oligonucleotide priming and used as a hybridisation probe to isolate four cosmids from an unaligned cosmid library of S. coelicolor M145 DNA. The probe failed to hybridise to the ordered cosmid library of Redenbach et al., 1996 (see below). Digestion of the four cosmids with BamHI revealed several restriction fragments of identical mobility, suggesting that each cosmid respresented the same genetic locus. Southern analysis of each of the cosmids using the same probe identified a common 4.5 kb BamHI fragment and a smaller hybridising fragment that ranged in size from 2.5 kb to 3.0 kb. The 4.5 kb fragment and the 3.0 kb BamHI fragment from cosmid GB10 were cloned in the BamHI site of pIJ2925 to yield pIJ6111 and pIJ6114, respectively. The restriction map of the contiguous 7.5 kb region is shown in FIG. 1. All four hybridising cosmids from the unaligned library were used as probes to identify their position in the combined physical and genetic map of the S. coelicolor chromosome. scbA was localised to the gap that lies at approximately 5 o'clock in the ordered cosmid library, in AseI fragment B, and next to cosmid 2H4 (H. M. Kieser personal communication; Kieser et al., 1992).

EXAMPLE 2 scbA Lies Adjacent to Genes Likely to be Involved in γ-butyrolactone Synthesis and Binding The nucleotide sequence of the 7.5 kb scbA region was determined (the sequence has been deposited under EMBL accession number AJ007731). Frame analysis (Bibb et al., 1983) revealed open reading frames (ORFs) with predicted translation products that showed homology to proteins likely (by analogy to the S. griseus system above) to be involved in both γ-butyrolactone synthesis and perception. ScbA (corresponding to nucleotide positions 2914–1970 of EMBL AJ007731 and 2142–1199 of FIG. 14) shares 64% amino acid sequence identity with AfsA, and about 40% identity with other AfsA homologues. The deduced amino acid sequence of ScbR, a protein encoded by a divergent ORF (corresponding to nucleotides 3032–3679 of EMBL AJ007731 and 2261–2908 of FIG. 14) which is adjacent to scbA, shows high levels of similarity to several γ-butyrolactone binding proteins. It is 56% identical to FarA of S. lavendulae FRI-5, and 45% identical to ArpA. Each of these homologues possesses an N-terminal DNA-binding domain that is also found in the TetR family of transcriptional repressors. The C-terminal regions of the ScbR family of proteins are relatively poorly conserved, and the inventors propose that this may reflect their ability to bind different γ-butyrolactones.

Downstream of ScbR, and transcribed in the opposite orientation, lies ScbB (nucleotides 3795–4529 of EMBL AJ007731 and 3024–3758 of FIG. 14), whose predicted product shows 50% amino acid identity to a C-5 ketoreductase from S. avermitilis (Ikeda et al., 1999); based on BLAST search (Altschul et al., 1997).

EXAMPLE 3

Transcription of scbA and scbR Occurs in a Growth-phase-dependent Manner

Figure 2B:
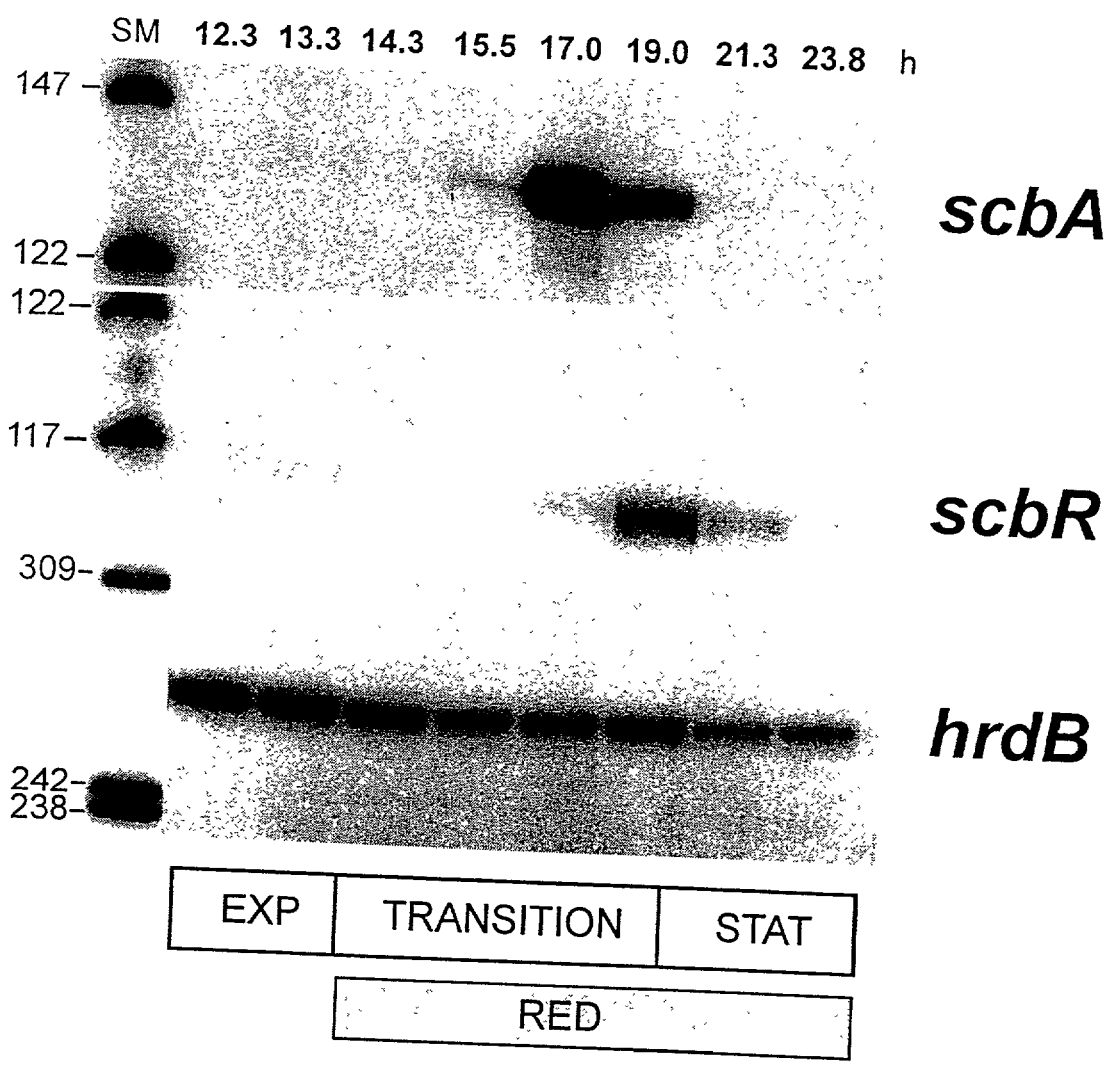
FIG. 2b S1 nuclease mapping of scbA, scbR, and the major sigma factor hrdB, using RNA isolated from a liquid time course of *S. coelicolor* M145 at the time (hours) indicated. The EXP, TRANSITION and STAT indicated the exponential, transition and stationary phases of growth, respectively, and the shaded box labelled RED denote the presence of undecylprodigiosin in the mycelium; SM, end-labelled HpaII-digested pBR322 size marker.

S1 nuclease protection experiments were carried out to determine the transcriptional start sites of scbA and scbR using RNA isolated from S. coelicolor M145 cultured in SMM to different stages of growth. A 259 bp PCR product (nucleotides 2786–3055 of EMBL, 2015–2284 of FIG. 14) labelled uniquely at the 5' end at position 2786/2015 was used as a probe for scbA transcripts, while a 280 bp PCR product (nucleotides 2894–3174 of EMBL, 2123–2403 of FIG. 14) labelled uniquely at the 5' end at position 3174/2403, was used as a probe for scbR. Putative transcriptional start sites were identified 46 nucleotides upstream of the likely translational start site of scbA, and 123–124 nucleotides upstream of that for scbR (FIG. 2a), i.e. at nucleotides 2960 and 2909-8, respectively (of the EMBL sequence, 2189 and 2138-7 of FIG. 14). Transcription of scbA, which was undetectable during exponential growth, increased markedly at late transition phase, and fell quickly as the culture entered stationary phase (FIG. 2b). The scbR transcript, while detectable during exponential growth, increased markedly in level in late transition phase, approximately one hour after the increase in the level of the scbA transcript. It also fell in stationary phase, after the decline in the level of the scbA transcript. The transcript of the major and essential sigma factor gene, hrdB, was used as a control, and was present at essentially constant levels through exponential growth, and fell gradually upon entry into stationary phase.

EXAMPLE 4

Figure 3A:
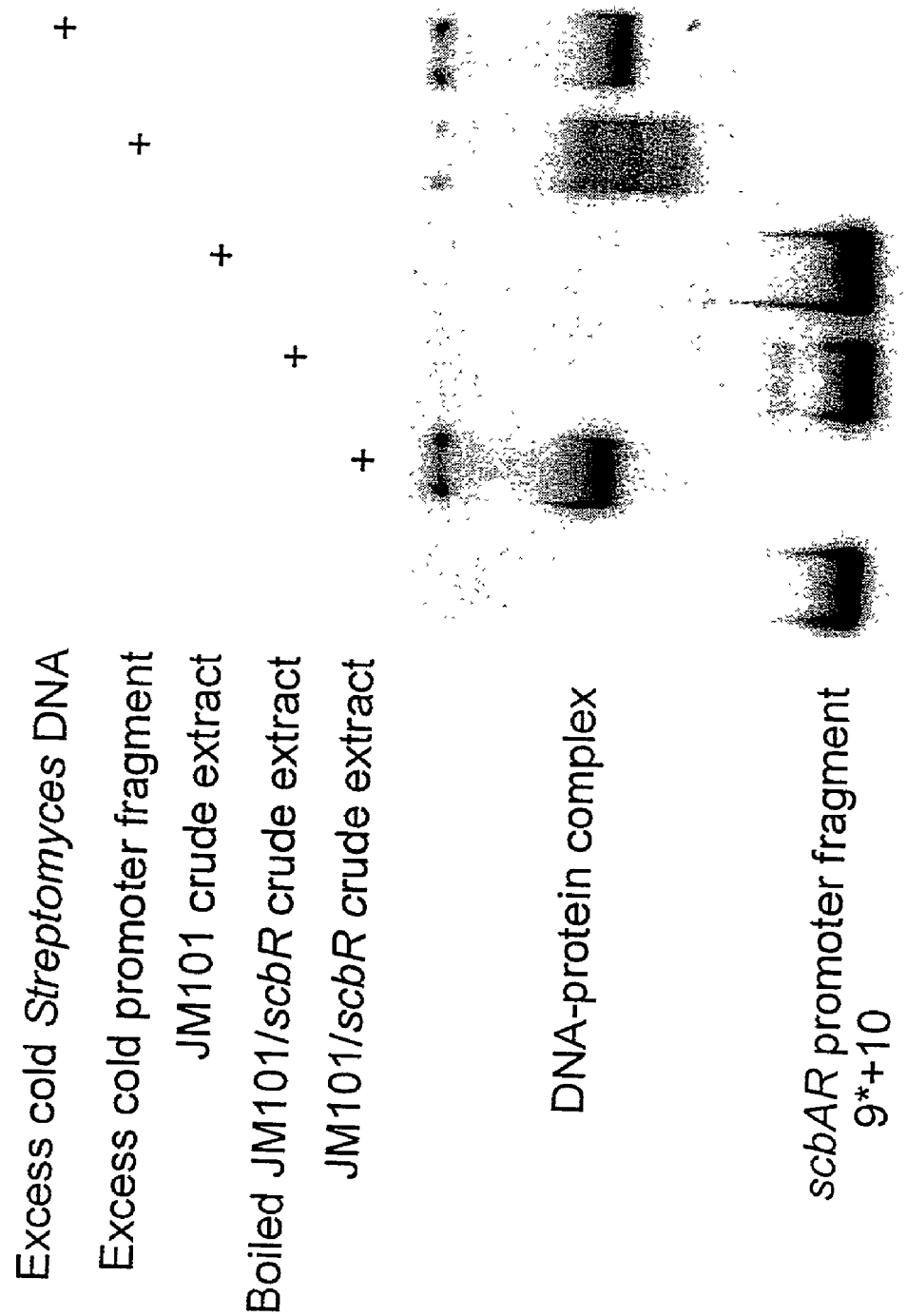
FIG. 3a Gel retardation experiment shown with crude extract of *E. coli* JM101 harboring scbR. Various crude extracts or unlabelled DNA fragments that were used in the experiment are indicated as +.
Figure 3B:
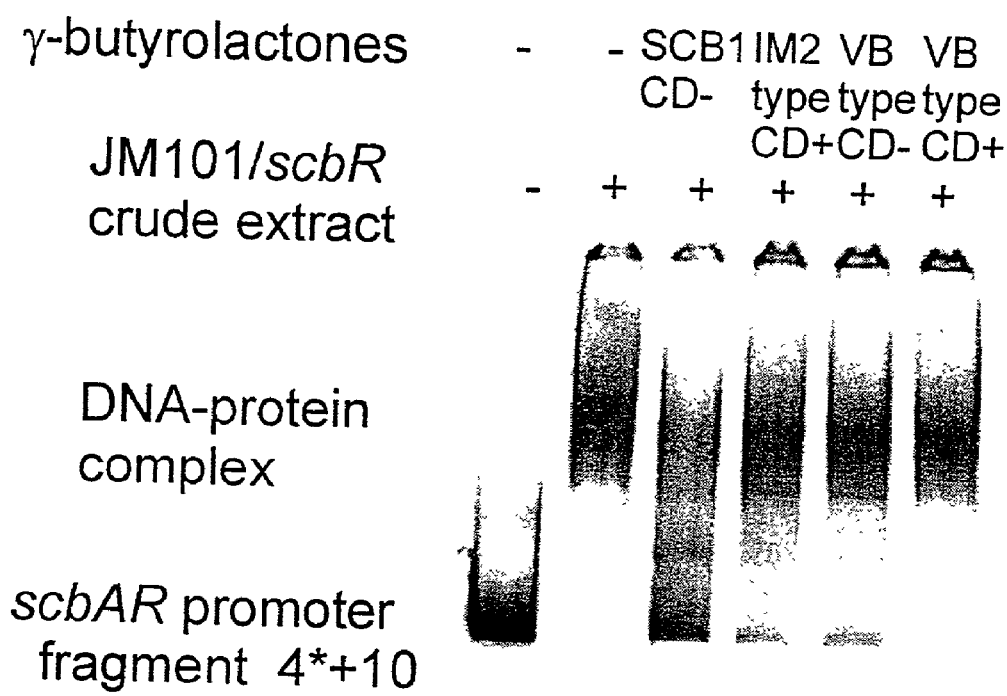
FIG. 3b Gel retardation experiments using E. coli JM101 crude extract harboring scbR and various γ-butyrolactones are indicated. CD denotes Circular Dichroism positive (+) or negative (−).

Binding of ScbR to the Promoter Regions of scbA and scbR is Prevented by SCB1 scbR was expressed in E. coli JM101 by cloning the 1.2 kb HincII-PvuII fragment containing scbR (FIG. 1) in pIJ2925, yielding pIJ6120. Extracts of JM101/pIJ6120 were then used in gel retardation assays with a 5' end-labelled PCR product that contained the scbA and scbR promoter regions (FIG. 3a). Retardation of the scbAR promoter fragment was readily detected on addition of the JM101/pIJ6120 extract (indicating binding of ScbR to the promoter region); no retardation was observed if the extract was first boiled, or with extract isolated from JM101 (FIG. 3b). Addition of an excess of unlabelled PCR product resulted in a reduction in the proportion of the labelled promoter-containing fragment that was retarded; however, no competition was apparent when unlabelled Streptomyces DNA (the plasmid pIJ922) was added, indicating a specific interaction between ScbR and the promoter DNA.

SCB1 (which, like A-factor, is a GBL) and its three chemically synthesized stereoisomers (Takano et al., 2000) were added to the gel retardation assays to assess their ability to influence the DNA-binding activity of ScbR. Formation of the DNA-protein complex was markedly reduced by addition of 1 μg of SCB1, while addition of equivalent amounts of each of the stereoisomers had little or no effect (FIG. 3c). Equivalent amounts of A-factor, IM-2 and VB also failed to inhibit the DNA-binding activity of ScbR (data not shown) indicating that the specificity of ScbR for SCB1, its cognate γ-butyrolactone, is high.

DNase I footprinting was used to determine the location of the DNA sites to which ScbR binds. Two protected regions were identified (FIGS. 4a and b); one lies at nucleotide position −4 to −33 with respect to the scbA transcriptional start site (i.e. nucleotides 2964–2993 of the EMBL sequence, 2193–2222 of FIG. 14), while the other lies at nucleotide position −41 to −67 with respect to the scbR transcriptional start site (i.e. nucleotides 2867/8–2841/2 of EMBL, 2096/7–2070/1 of FIG. 14). Dilution of the JM101/pIJ6120 extract suggests that ScbR has a stronger affinity for the binding site upstream of scbA than for that upstream of scbR.

EXAMPLE 5

Deletion of scbA Abolishes γ-butyrolactone Synthesis, but Results in Overproduction of Act and Red, while Deletion of scbR also Abolishes γ-butyrolactone Synthesis, but Causes Delayed Red Production To assess the role of scbA and scbR in antibiotic production in S. coelicolor, in-frame deletions were made in each gene. Mutant scbA and scbR alleles were constructed in which most of the scbA and scbR coding regions (amino acids 42–276 out of 315, and 33–178 out of 216, respectively) were deleted. The mutant scbA and scbR alleles were cloned in the E. coli plasmid pKC1132, yielding pIJ6140 and pIJ 6134, respectively (FIG. 1), and introduced into S. coelicolor strain M145 by conjugation; selection for apramycin resistance ensured integration of the non-replicating plasmids into the streptomycete chromosome by homologous recombination. After three rounds of sporulation on non-selective medium, apramycin-sensitive segregants were screened by PCR, and putative scbA (M751) and scbR (M752) deletion mutants further confirmed by Southern analysis.

Figure 5A:
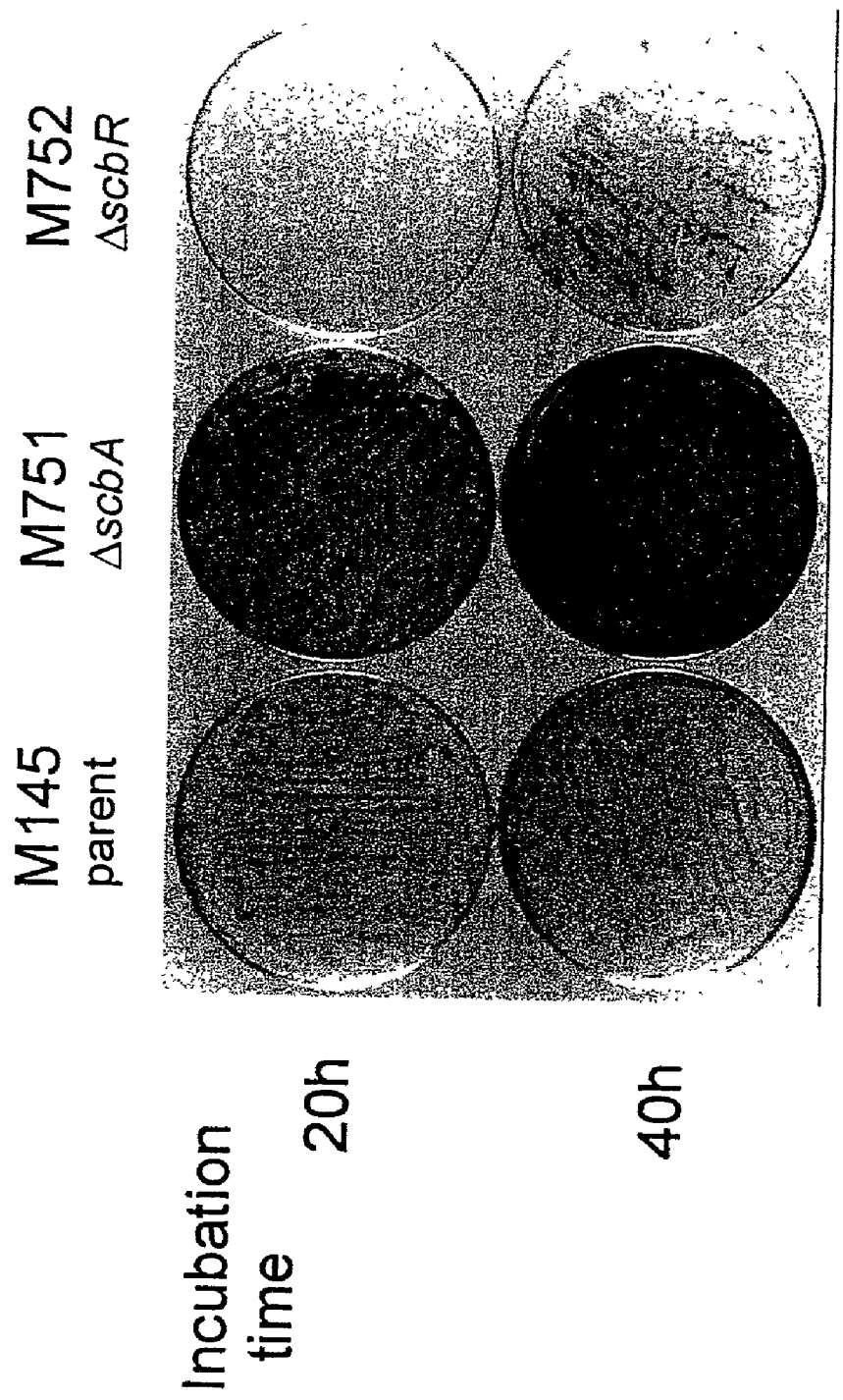
FIG. 5a Effect of deletion of scbA or scbR on antibiotic production in solid grown S. coelicolor M145. Confluent lawn of M145, M751 and M752 were grown on SMMS at 30° C. for 20 h (top plates) or 40 h (bottom plates).

Confluent lawns of the parental strain M145, M751 (ΔscbA) and M752 (ΔscbR) were grown on nitrogen-limited SMMS agar plates to assess the affect of each deletion (FIG. 5). After 20 h, Red production had just begun in M145, while Act synthesis was undetectable. In contrast, M751 had produced large amounts of both Red and Act (detectable by exposing the agar plate to ammonia fumes, which resulted in the blue pigmentation characteristic of Act), and M752 had failed to produce either antibiotic. By 40 h, the overproduction of both Act and Red by M751 was very marked, while Red production was noticeably delayed and Act production detected earlier (FIG. 5A) in M752 as compared to M145. The mutant phenotypes were also observed on rich R5 agar and on phosphate-limited R2 agar, but both mutants resembled the parental strain on rich SFM agar and minimal medium containing mannitol as carbon source. Growth of the strains in SMM liquid medium gave phenotypes that corresponded to those observed with SMMS agar.

Figure 5B:
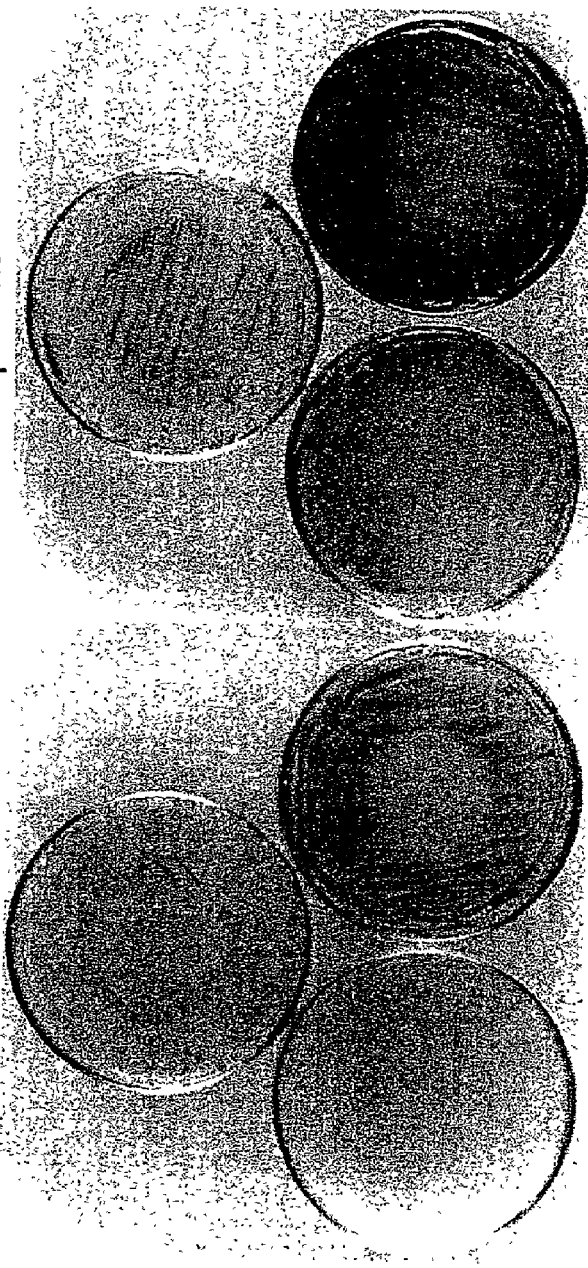
FIG. 5b Effect of deletion of scbA or scbR on response to SCB1, a γ-butyrolactone. Bioassay using spore suspension of M145(top), M751(left bottom) and M752(right bottom) as indicator strain and spotted with 1 µg of SCB1. The plates were incubated at 30° C. for 20 h (left panel) or 40 h (right panel).

To assess the ability of the mutants to respond to SCB1, 1 μg of chemically synthesised SCB1 (Takano et al (2000) supra) was spotted onto confluent lawns of M751, M752 and M145 (FIG. 5b). While M145 responded in the expected way to exogenous SCB1, M752 did not respond. Since M751 precociously overproduced both Act and Red, it was not possible to determine whether it had retained the ability to respond to the the γ-butyrolactone; however, the inhibitory effect of high concentrations of SCB1 on antibiotic production in M145 (the lighter halo surrounding the point of application; Takano et al., 2000) was also observed with M751, suggesting that it had indeed retained the ability to sense SCB1.

Figure 6:
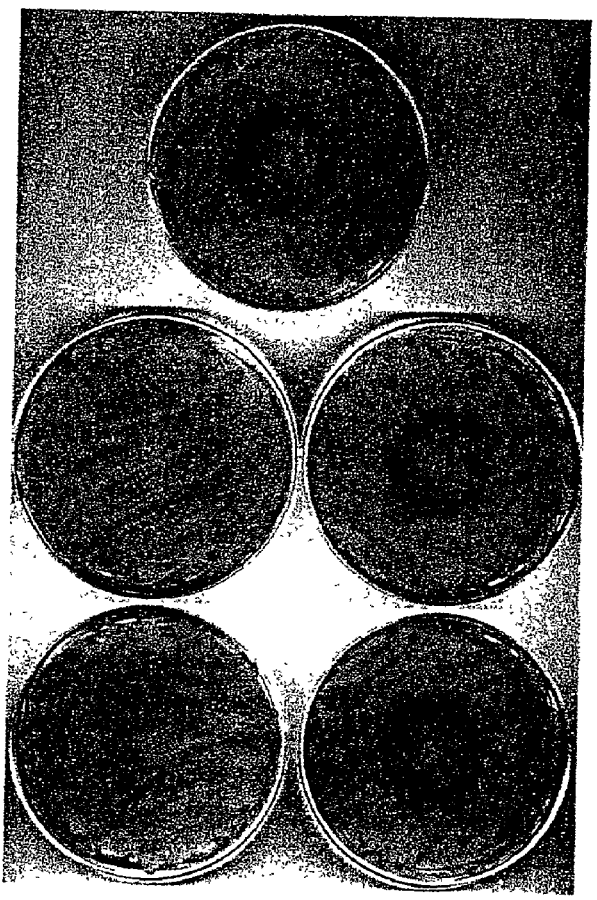
FIG. 6 Effect of deletion of scbA or scbR on the production of γ-butyrolactones with antibiotic stimulatory activity. Bioassay of ethyl acetate extracts from SMMS solid cultures of M145 (pset152) (top), M751 (pset152) (left side) and M751 complemented with scbA (right side), M752 (pset152) (right side) and M752 complemented with scbR (left side). In each case the indicator lawn is M145 and grown on SMMS at 30° C. for 30 h.

The ability of the mutants to produce compounds, including SCB1, with antibiotic stimulatory activity was assessed using the standard bioassay (the ability to induce precocious Act and Red production in a lawn of M145). M751, M752 and M145 were grown on SMMS agar and in SMM liquid medium, and samples of agar and culture supernatant from different growth phases were extracted with ethyl acetate. Neither mutants produced stimulatory activity (FIG. 6) regardless of growth phase or medium To confirm that the mutant phenotypes reflected the absence of a functional scbA or scbR, rather than a mutation elsewhere in the genome, scbA or scbR were reintroduced into M751 and M752, respectively. A 1194 bp PCR product containing scbA and its promoter (FIG. 1, pIJ6143), and a 1.3 kb BglII fragment containing scbR and its promoter (FIG. 1 pIJ6135), were cloned in E. coli in pSET152 yielding pIJ6147 and pIJ6135, respectively. The plasmids were introduced into the corresponding S. coelicolor mutant by conjugation and selection for apramycin resistance, and integration at the ΦC31 attachment site was confirmed by Southern hybridisation. All of the mutant phenotypes were restored to those observed in M145 (FIG. 6 for restoration of SCB1 synthesis).

Figure 7B:
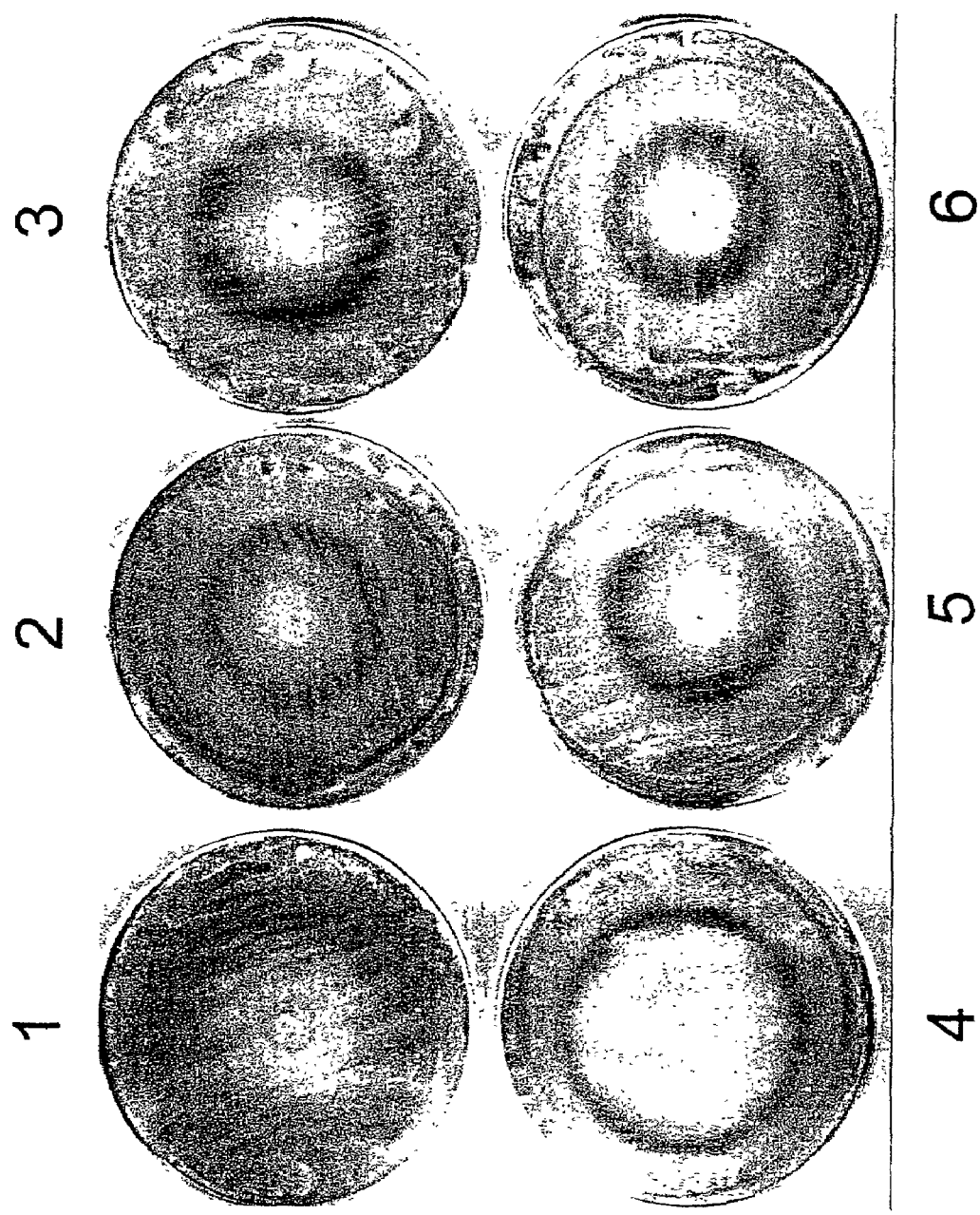

EXAMPLE 6 scbR Regulates the Transcription of Both scbR and scbA, and scbA is Required for the Transcription of scbA Since ScbR binds in vitro to the scbA and scbR promoter regions, and given that SCB1 is able to prevent such binding, the effect of the scbA and scbR deletions on transcription of each of the genes in vivo was assessed. RNA was isolated from SMM-grown M145, M751 and M752 cultures at different stages of growth and subjected to S1 nuclease protection experiments (FIG. 7a). While the scbA transcript was readily detected in early transition phase cultures of M145, it was absent in M751 (ΔscbA) and barely detectable in M752 (ΔscbR) regardless of growth phase, suggesting that both scbA and scbR are required for induction of scbA transcription. While the level of the scbR transcript increased during late transition and early stationary phase in M145, it was markedly diminished in the scbA mutant, and highly abundant in exponential and early transition phase in the scbR mutant. These observations suggest that scbR negatively regulates its own transcription, and that relief of this repression requires scbA. Transcription of hrdB, the major and essential sigma factor of S. coeliclor, was monitored as a control. Antibiotic production (FIG. 7a) and production of antibiotic stimulatory factors (FIG. 7b) were also assessed at the times of RNA extraction. The commencement of factor synthesis in M145 corresponded well with the increase in the scbA transcription.

EXAMPLE 7

Addition of SCB1 to M751 (ΔscbA) Stimulates scbR Transcription but Fails to Restore scbA Transcription To assess the effect of addition of exogenous SCB1 on scbA and scbR expression in the ΔscbA mutant, in which transcription of both genes is markedly impaired, chemically synthesised SCB1 was added at a final concentration of 31 ngml$^{-1}$ to a mid-exponential phase (OD$_{450\ nm}$=0.5) culture of M751. While there was a marked increase in the level of scbR transcription, scbA transcription in the ΔscbA mutant was not restored (FIG. 8).

EXAMPLE 8

Deletion of scbA in S. lividans 1326 Abolishes Gamma-butyrolactone Synthesis and Results in Increased Production of Act and Red by Strains Containing the Multi-copy Plasmids pIJ68 or pIJ6014

The mutant scbA allele from S. coelicolor (described in example 5) was introduced into S. lividans 1326 using pIJ6140. Integration of the non-replicating plasmid was selected using apramycin. After three rounds of non-selective growth (on SFM agar) colonies were screened for sensitivity to apramycin (indicating loss of the plasmid due to a second homologous recombination event). 4 apramycin-sensitive colonies were identified among 3,000 colonies screened. PCR analysis of chromosomal DNA produced amplified DNA fragments consistent with that observed from wild type chromosomal DNA for three colonies, whereas the fourth colony yielded a smaller DNA fragment consistent with the in-frame deletion allele. Southern hybridisation experiments of chromosomal DNA digested either with NcoI or a mixture of BglII and PstI produced hybridising bands consistent with the results expected for the wild type arrangement for the first three colonies and the mutant for the fourth colony, which was designated S. lividans M707. When this strain was grown on agar medium no ScbA was detected, whereas it was demonstrably produced by the wild type S. lividans 1326 strain.

Figure 12:
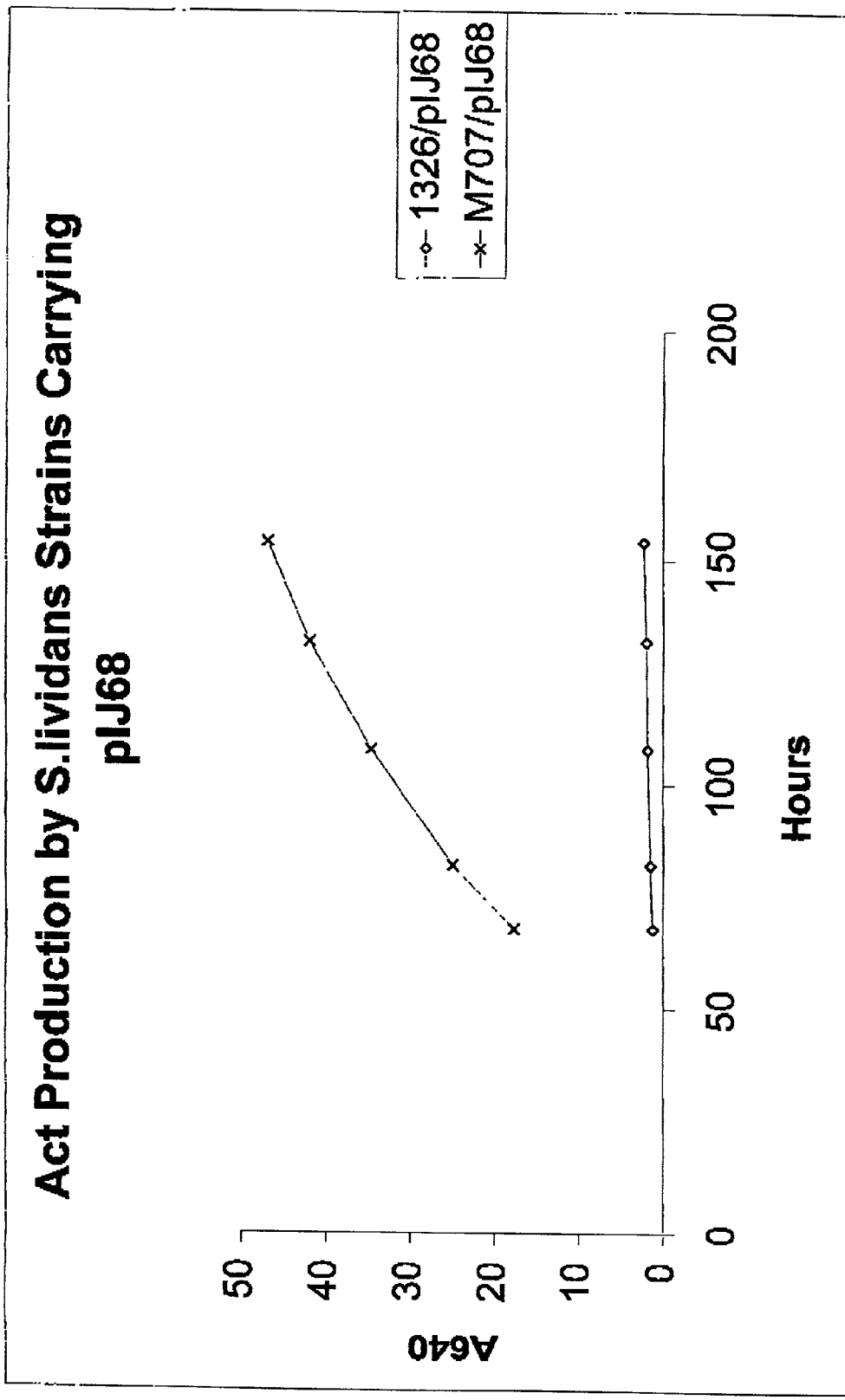
FIG. 12 Production of Act by S. lividans strains carrying pIJ68.
Figure 13:
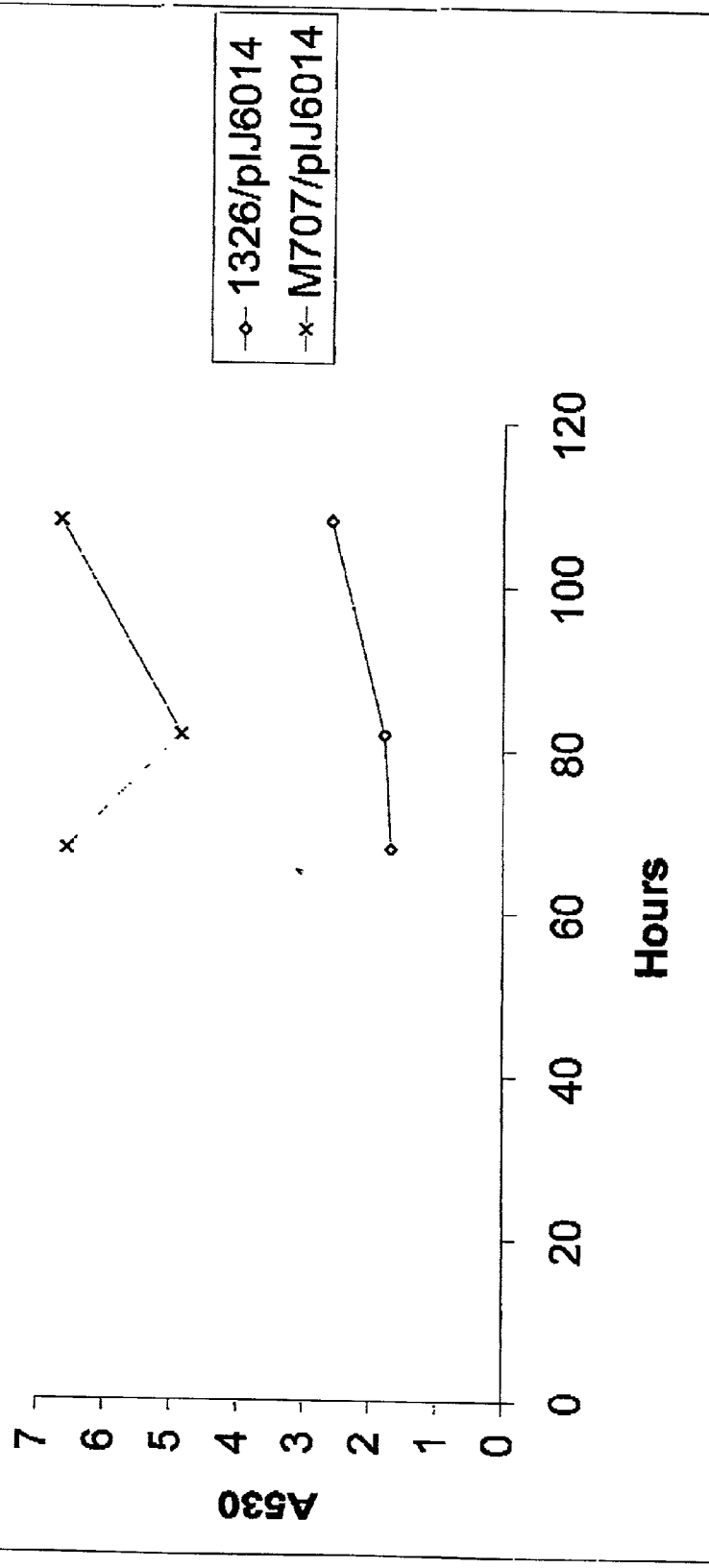
FIG. 13 Production of Red by S. lividans strains carrying pIJ6014.

Spores of the M707 strain were inoculated into liquid YEME medium (containing 0.5% glycine and 5 mM MgCl$_2$)

and grown with shaking at 30° C. for 2 days. The mycelium was collected by centrifugation and used to produce protoplasts, which were transformed with pIJ68 (actII-orf4) (Passantino R et al (1991) J. Gen Microbiol 137:2059–2064), pIJ6014 (redD) (Takano E et al (1992) 6(19): 2797–2804) or pIJ486 (vector control) (Ward J M et al (1986) Mol Gen Genet 203:468–478). Thiostrepton-resistant transformants were selected and tested in shake flask fermentation experiments. Spores of the transformed strains were streaked on SFM agar (containing 50 µg/ml of thiostrepton) and incubated at 30° C. for 4–5 days. Spores were harvested and inoculated into spring flasks with 50 ml YEME (containing 50 µg/ml of thiostrepton). After two days incubation at 30° C. the mycelium was collected by centrifugation and resuspended in fresh spring flasks containing phosphate-limited Evans medium with 20 µg/ml of thiostrepton. Incubation was continued at 30° C. for a further seven days with 1 ml samples being removed for assessment of antibiotic production. The Act or Red production is shown in FIGS. 12 and 13 and confirmed the findings observed for S. coelicolor that antibiotic synthesis was precocious and elevated. Approximately three to four times the concentration of Red was observed compared to the S. lividans 1326 strain carrying pIJ6014. For Act the concentration difference was five to ten fold for the pIJ68-containing strains. Moreover, when dry cell weight (DCW) measurements were made it was noted that the M707/pIJ68 strain produced less mycelial material than the S. lividans 1326/pIJ68 under these conditions. Thus, when expressed as concentration of Act produced per gram DCW, the M707 strain produced 121 compared to the control 1.5.

(Plasmids pIJ68/pIJ6014 were introduced into S. lividans to supply the pathway specific transcriptional activator genes for Act/Red production. No equivalent plasmids are required in S. coelicolor.)

These strains were further tested for their ability to produce Act in 1 liter liquid batch fermentations in stirred tank bioreactors using a modified phosphate-limited Evans medium (with $NH_4Cl$ instead of $NaNO_3$). The M707/pIJ68 strain produced 10 g/l of act compared to the S. lividans 1326/pIJ68 control, which made 5 g/l.

DISCUSSION

Two genes, scbA and scbR, have been isolated from S. coelicolor A3(2) and respectively show high homology to the afsA and arpA genes of S. griseus, which encode A-factor synthetase and A-factor binding protein. The in-frame deletion mutant of scbA overproduces both antibiotics, while the in-frame deletion mutant of scbR is delayed in RED production and does not produce γ-butyrolactones which (in the wild-type strain) cause precocious RED and ACT production. These phenotypes are most surprising considering the high homology of the genes to the A-factor system in S. griseus.

Ohnishi et al. (1999) reported the cascade for the streptomycin production in S. griseus, triggered by A-factor. ArpA (A-factor binding protein) binds to the promoter region of adpA (a transcriptional activator for streptomycin production) and represses the transcription arpA from the promoter region by binding to it. Thus adpA is transcribed and activates the streptomycin biosynthetic cluster via strR (streptomycin pathway-specific activator) and the antibiotic is produced. To corroborate their model, the afsA mutant (equivalent to the scbA mutant of the present work) produces neither streptomycin nor A-factor. Also the arpA mutant (equivalent to the scbR mutant of the present work) overproduces antibiotics; A-factor production is not effected. These are the reverse phenotypes compared to those of the in-frame deletion mutants of the present work using S. coelicolor. The inventors propose that ?-butyrolactones are involved in antibiotic production differently in S. coelicolor, compared with the known GBL model of S. griseus.

The two genes scbA and scbR are located next to each other in the S. coelicolor genome, which is not the case for the equivalent genes of S. griseus (afsA and arpA). afsA is located at the end of the linear chromosome (Lezhava et al., 1997) thus being easy to mutate to obtain deletion mutants and arpA is located elsewhere on the chromosome (Ohnishi et al., 1999). On the other hand, like the arrangement in S. coelicolor, the homologues of afsA in S. virginiae (barX) and S.fradiae (farX) are located next to genes encoding γ-butyrolactone binding proteins (barA and farA respectively) (Nakano et al., 1998; Waki et al., 1997). In S. virginiae, a mutation in barA (a homologue of arpA) results in precocious virginiamycin production, consistent with the role of arpA in S. griseus, yet it abolishes VB production (Nakano et al., 1998). The inventors propose, therefore, that the juxtaposition of streptomycete genes encoding GBL synthetases and GBL binding proteins may be reflective of a different antibiotic regulatory system from that of the S. griseus model (possibly in some cases additional to such a regulatory system), namely one in which functional deletion of the gene encoding the GBL binding protein leads not to overproduction of antibiotic (as in the S. griseus system), but under- or delayed production. Moreover, they suggest that in such systems, functional deletion of the GBL synthetase leads to overproduction of the antibiotic (in contrast to abolition of streptomycin production in S. griseus).

MATERIALS AND METHODS

Bacterial Strains, Plasmids, and Growth Conditions

S coelicolor A3(2) strain M145 (Hopwood et al., 1985), M751 and M752 (this study) were manipulated as previously described (Hopwood et al., 1985). E.coli K-12 strains JM101(Sambrook et al., 1989) and ET12567 (MacNeil et al., 1992) were grown and transformed according to Sambrook et al., (1989). Vectors used were pIJ2925 (Janssen and Bibb., 1993), pKC1132 (Bierman et al., 1992), pset152 (Bierman et al, 1992), pBluescript SK$^+$ (Stratagene), pGEM-T vector (Promega). SMM is the modified minimal medium of Takano et al., (1992); it lacks $(NH_4)_2SO_4$ and has 0.25 mM $NaH_2PO_4$, 0.25 mM $K_2HPO4$ instead of 0.5 mM each. SMMS is a modified solid version of SMM, as described above. SFM medium was used to make spore suspensions and for use in conjugation with E.coli ET12567 containing the RP4 derivative pUZ8002 (Flett et al., 1997).

PCR

The synthetic oligonucleotides oligo1; 5'-GACCACGT(CG)CC(CG)GGCATG (SEQ ID NO: 1) and oligo2; 5'-GTCCTG(CG)TGGCC(CG)GT(CG)AC(CG)CG(CG) AC (SEQ ID NO: 2) (bracketed nt indicate positions of degeneracy) were used in the PCR (Erlich, 1989) to amplify the internal segment of scbA from S. coelicolor M145 total DNA (FIG. 2a). The reaction mixture contains: 10× reaction mixture supplied by Boehringer Mannheim, 200 µM final concentration of four dNTPs, 5% final concentration of DMSO, 50 pmol of each primer, 50 ng of chromosomal DNA in a final volume of 100 µl. After denaturation by boiling 5 mm, 2.5 U of Taq polymerase was added and subjected to 30 cycles of denaturation at 94° C. for 50 sec, annealing at 55° C. for 40 sec and extension at 72° C. for 40 sec, and then incubated at 72° C. for 10 min. PCR products were analyzed on a 2% w/v agarose gel electrophoresis.

To complement M751, scbA coding sequence with its promoter region was amplified by PCR from *S. coelicolor* M145 cosmid GB10 DNA. Two synthetic oligonucleotides 5'-GCCAGCAGGTGGGCGACCTGAC (1796 nt position; SEQ ID NO: 3) and 5'-GATCGCCCGGTCCTGCTTGGC-CATG (3055 nt position; SEQ ID NO: 4) were used. The PCR conditions were as stated above except the High Fidelity Kit (Beoringher Mannheim) was used and the PCR cycle was reduced to 20. The PCR product was purified by a Sephadex G-50 (Pharmacia) spin column then ligated to the pGEM easy vector (Promega) and transformed to JM101. The sequence of the transformant was confirmed by using the ABI automated sequencer and Big Dye dye terminator cycle sequencing kit (Perkin Elmer).

Nucleotide Sequencing

The nucleotide sequencing of the 7.5 kb scbA region was sequenced by the ABI automated sequencer and using the Big Dye dye terminator cycle sequencing kit (Perkin Elmer) as recommended by the suppliers, except in the PCR reaction, final concentration of 5% DMSO was added to the reaction mixture. The sequence was submitted to the databases (EMBL AJ007731) and sequenced on both strands.

S1 Nuclease Mapping

For each S1 nuclease reaction, 30 or 40 μg of RNA were hybridized in NaTCA buffer (Murray, 1986; Solid NaTCA (Aldrich) was dissolved to 3M in 50 mM PIPES, 5 mM EDTA, pH7.0) to about 0.002 pmol (approximately $10^4$ Cerenkov counts min $10^{-1}$) of the following probes. For scbA the synthetic oligonulceotide 5'-TATCCAGCTGACCGG-GAACGCGTC (SEQ ID NO: 5), corresponding to the region within the coding region of scbA was labelled with [$^{32}$P]-ATP using T4 polynucleotide kinase uniquely at the 5' end of the oligonucleotide, then used in the PCR reaction with the unlabelled oligonucleotide 5'-ATCGCCCGGTC-CTGCTTGGCCATG (SEQ ID NO: 6) which corresponds to a region upstream of the scbA promoter region to generate a 259 bp probe. For scbR, the synthetic oligonulceotide 5'-AAGTAGAGGGCTCCCTTGGTCA (SEQ ID NO: 7), corresponding to the region within the coding region of scbR was labelled with [$^{32}$P]-ATP using T4 polynucleotide kinase uniquely at the 5' end of the oligonucleotide, then used in the PCR reaction with the unlabelled oligonucleotide 5'-CAAAACTACTGCTTCGGGCATG (SEQ ID NO: 8) which corresponds to a region upstream of the scbR promoter region to generate a 280 bp probe. Both PCR reactions were done using M145 total DNA as template. For hrdB, the probe was made as previously described (Buttner et al., 1990). Subsequent steps were as described by Strauch et al. (1991).

Gel Retardation Assays and Dnase I Footprinting Studies 50 pmol of the synthetic oligonucleotides 5'-CTGCAC-CCTGGTCCGGTGGACA (SEQ ID NO: 9) and 5'-ATCGC-CCGGTCCTGCTTGGCCATG (SEQ ID NO: 10) were both labelled with [$^{32}$P]-ATP using T4 polynucleotide kinase uniquely at the 5' end of the oligonucleotide, then used in the PCR reaction with the unlabelled synthetic oligonucleotide corresponding to the other primer to generate a 244 bp DNA fragment. The PCR amplified fragment was further purified by Qiagen PCR purification kit. The gel retardation assay reaction mixture contains; 5× gelretardation buffer (125 mM HEPES pH7.5, 20 mM DTT, 10 mM ATP, 20% glycerol) 200 mM KCl, 0.16 μg/μl calf thymus DNA, and 0 to 15 μl of JM101 crude extract containing ScbR protein in a final volume of 12.5 to 25 μl. The final concentration of DNA fragments used was 2.5 ng/ml. The mixture was incubated at room temperature for 10 min then 2 μl of dye (50% (w/v) glycerol with BPB in TE) was added to the mixture and 10 μl was loaded to a 5% (w/v) non-denaturing polyacrylamide gel buffered with TBE. SCB1 was added to the reaction mixture either prior to incubation, or after 10 min of incubation then incubated for further 10 min.

Dnase I footprinting studies were performed as described by Drapal and Sawer, (1995). 25 ng/ml of DNA fragments were incubated in gel retardation assay mixture (final total volume 25 μl) with varying concentration of protein. After incubation, 25 μl of 10 mMMgCl and 5 mMCaCl$_2$ was added. After 1 min 0.1 unit of Dnase I (Boerhinger Mannheim) was added and incubated for 45 sec then the reaction terminated by adding 30 μl of stop solution (20 mMEDTA, 200 mM NaCl, 1% SDS (w/v), 250 μg ml$^{-1}$ tRNA). The DNA fragments were purified by phenol/chloroform extraction and precipitated with three volumes of ethanol. The precipitants were resuspended in loading buffer and ran on a 6% (w/v) sequencing gel. Sequencing reactions were performed using the synthesised oligonucleotides as primers on double strand DNA and by using a dideoxy sequencing kit (Taq Track, Progema).

Crude Extract Isolation

An overnight culture of *E. coli* JM101 harboring pIJ6120 was diluted 1/100 and innoculated into 25 ml LB media. The culture was grown at 37° C. for approximately 3.5 hr or until the cultures were at 1.0 $OD_{600\ nm}$. The culture was then induced with final concentration of 1 mM IPTG. After further 3 hr of growth, the cells were harvested by centrifugation and the cell pellet was washed twice with buffer (50 mM Tris pH7.0, 1 mM EDTA, 1 mM DTT, 100 mM PMSF), resuspended in 500 μl of buffer and disrupted by sonication. The cell lysate was then clarified by centrifugation and the supernatant was used as crude extracts.

Isolation of γ-butyrolactones, Bioassay and HPLC Analysis

γ-butyrolactones were isolated from liquid or solid media by extracting the culture supernant or the agar with ethylacetate. The ethylacetate was evaporated and the sample was resuspended in 100% methanol for use in a bioassay or for HPLC analysis. Bioassay and HPLC analysis were conducted as described previously (Takano et al., 2000).

Construction of an In-frame Deletion Mutant of scbA and scbR

The in-frame deletion mutant of scbA was constructed by digesting pIJG136 which contains a 1.4 kb flanking DNA of scbA in pIJ2925 (FIG. 1) with BamHI and end filled using Klenow fragment and ligated with a 1.1 kb PvuII-HincII fragment from pIJ6111. The transformants were analysed to find the PvuII-HincII fragment was inserted with the internal PstI site at the EcoRI side of the multiple cloning site of pIJ6136 and designated pIJ6137. The BglII fragment of pIJ6137 was inserted into the BamHI site of pKC 1132 (Bierman et al., 1992) to give pIJ6140 (FIG. 1). The inframe deletion mutant of scbR was constructed by PCR using the High Fidelity Kit (Beoringher Mannheim) with a universal primer and 5'-CATCTGCAGCGTGATCGTG-GCAGCTTGGTAG (3130 nt position; SEQ ID NO: 11) primer designed to give a 1.059 kb DNA fragment flanking scbA as described earlier. A PstI site was designed into the end of this fragment to enble ligation with a PstI site internal of scbR. pIJ6111 was used as template for the PCR reaction and the amplified product was cloned into pGEM-T vector (Promega) to give pIJ6148. The sequence of the PCR amplified insert of pIJ6148 was confirmed by ABI automated sequencing. The BamHI-KpnI 3 kb fragment of pIJ6111 was cloned into pBluescript SK+ (Stratagene) to give pIJ6131. The 1.059 kb BamHI-PstI fragment was isolated from pIJ6148 and cloned into the BamHI-PstI digested pIJ6131 to give pIJ6152. pIJ6152 was then digested with KpnI and blunt ended then further digested with BamHI. This 2.48 kb DNA fragment was cloned into pKC1132 digested with BamHI and EcoRV to give pIJ6134 (FIG. 1). Both plasmids were introduced into the methylation deficient E. coli strain ET 12567 containing the RP4 derivative pUZ8002 (Paget et al., 1999) and transferred into S. coelicolor M145 by conjugation. Single-crossover exconjugants were selected on SFM containing apramycin. Three such single colonies were then taken through three rounds of non-selective growth on SFM to promote the second crossover. Spores were then plated for single colonies which were scored for apramycin sensitivity. Deletions within scbA and scbR were confirmed by PCR using primers correponding to flanking sequences, and by Southern hybridisation. For scbA, nine out of 20 apramycin sensitive colonies were deleted for scbA while 11 had reverted to wildtype. For scbR, 4 out of 20 apramycin sensitive colonies were deleted for scbR while 16 reverted to wildtype. The scbA and scbR deletion mutants were called M751 and M752, respectively.

To complement the mutants, a 1194 bp PCR product (subsequently sequenced) containing the entire scbA coding region with its promoter (pIJ6143) and a 1.3 kb BglII fragment containing the entire region of scbR with its promoter (pIJ6135) (FIG. 1) was cloned into a conjugative vector pset152 (Bierman et al, 1992), which integrates into the chromosome of S. coelicolor by site-specific recombination at the bacteriophage ΦC31 attachment site, attB (Kuhstoss, E. et al 1991). The resulting plasmids, pIJ 6147 and pIJ6135 (FIG. 1), respectively were transferred into S. coelicolor by conjugation via the E. coli donor ET 12567 containing the RP4 derivative pUZ8002 (Paget et al., 1999). Exconjugants were purified by single-colony isolation, and the plasmid integration were confirmed by southern hybridization.

Other Methods

Antibiotic production was determined by extracting actinorhodin and undecylprodigiosin as described previously (Strauch et al., 1991). RNA was isolated as described in Strauch et al., (1991). Southern hybridisation was done as previously described (Hopwood et al., 1985). Probes for southern hybridisation were made by labelling DNA fragments or PCR products with $^{32}P$ by random oligolabelling (Pharmacia).

Further protocols are performed according to standard reference texts, such as Hopwood et al. (1985) and Sambrook et al. (1989), or later editions thereof.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims. In particular, although the claims refer to certain species of Streptomyces, it will be readily apparent that the teaching of the invention may be applied to other species of Streptomyces, especially species which are closely related to the species referred to in the claims and/or species having a similar arrangement of scbA and scbR genes (or their homologues).

REFERENCES

Altschul, S. F., et al. (1997) Nucleic Acids Res. 25: 3389–3402
Ando, N., et al. (1997) J. Antibiot 50: 847–852.
Bate, N., et al. (1999) Chemistry & Biology 6: 617–624.
Bibb, M. J., et al. (1984) Gene 30: 157–166.
Bierman, M., et al. (1992) Gene 116: 43–49.
Buttner, M. J., et al. (1990) J Bacteriol 172:3367–3378.
Chater, K. F. and Bibb, M. J. (1997) Regulation of bacterial antibiotic production. In Biotechnology, volume 7: Products of Secondary Metabolism. Kleinkauf, H. and von Döhren, H. (eds).
Weinheim, VCH, Germany. pp 57–105.
Chater K. F., and Hopwood D. A. (1993) Streptomyces. In Bacillus subtilis and other Gram-positive Bacteria: Biochemistry, Physiology, and Molecular genetics. Sonenshein, A. L., Hoch, J. A., and Losick, R. (eds.). Washington, D.C.: American Society for Microbiology, pp. 83–89.
Chakraburtty, R., et al. (1996) Mol Microbiol 19:357–368.
Chakraburtty, R. and Bibb, M. (1997) J Bacteriol 179: 5854–5861.
Drapal, N. and Gary, S. (1995) Mol Microbiol 16:597–607.
Erlich, H. A. (1989) PCR Technology. New York: Stockton Press.
Fouces, R. et al. (1999) Microbiol 145: 855–868.
Flett, F., et al. (1997) FEMS Microbiol Lett 155: 223–229
Gramajo, H. C., et al. (1993) Mol Microbiol 7:837–845.
Hara, O., et al. (1983) J Gen Microbiol 129:2939–2944.
Hopwood, D. A., et al. (1985) Genetic Manipulation of Streptomyces: A Laboratory Manual. Norwich: John Innes Foundation.
Hopwood, D. A., et al. (1995) Genetics of antibiotic production in Streptomyces coelicolor A3(2). In: Genetics and Biochemistry of Antibiotic Production. Vining, L. (ed) Butterworth-Heinemann, Newton, Mass., USA. pp. 65–102.
Horinouchi, S., and Beppu, T. (1994) Autoregulators. In: Genetics and Biochemistry of Antibiotic Production. Vining, L. (ed) Butterworth-Heinemann, Newton, Mass., USA. pp. 103–119.
Horinouchi, S., et al. (1985) J Antibiot 36:636–641.
Horinouchi, S., et al. (1989) J Bacteriol 171:1206–1210.
Ikeda, H., et al. (1999) Proc. Natl. Acad. Sci. 17: 9509–9514
Janssen, G. R., and Bibb, M. J. (1993) Gene 124: 133–134.
Kieser, H. M., et al. (1992) J Bacteriol 174:5496–5507.
Kieser, H. M., et al. (eds) (2000) Practical Streptomyces Genetics, John Innes Foundation, Crowes Printers, Norwich, England.
Kinoshita, H., et al. (1997) J Bacteriol 179: 6986–93.
Kitani, S., et al. (1999) J Bacteriol 181: 5081–5084.
Kondo, K., et al. (1989) J. Antibiot 42: 769–778.
Kuhstoss, S., and Rao, R. N. (1991) J Mol Biol 222: 897–908.
Lezhava, A., et al. (1997) Mol Gen Genet 253: 478–483.
MacNeil, D. J., et al. (1992) Gene 155: 119–125.
Miyake, K., et al. (1990) J. Bacteriol 172: 3003–3008.
Mori, K. (1983) Tetrahedron Lett 39:3107–3109.
Murray, et al. Anal Biochem 158(1): 165–70.
Nakano, H., et al. (1998) J Bacteriol 180: 3317–3322.
Nihira, T., et al. (1988) J Antibiot 41:1828–1837.
Okamoto, S., et al. (1995) J. Biol Chem 270: 12319–12326.
Onaka, H., et al. (1995) J Bacteriol 177:6083–6092.
Onaka, H., and Horinouchi, S. (1997) Mol Microbiol 24:991–1000.
Onaka, H., et al. (1998) Mol Microbiol 28: 743–753.
Ohnishi, Y., et al. (1999) Mol Microbiol 34:102–111.

Paget, M. S. B, et al. (1999) *J Bacteriol* 181:204–211.
Redenbach, et al. (1996) *Mol Bicrobiol* 21: 77–95.
Rothstein, et al. (1987) *Gene* 53(2–3): 153–61.
Ruengjitchatchawalya, M., et al. (1995) *J Bacteriol* 177: 551–557.
Sambrook, J., et al. (1989) *Molecular Cloning. A Laboratory Manual.* Cold Spring Harbor, N.Y.: Cold Spring Harbor Laboratory Press.
Sato, K., et al. (1989) *J Ferment Bioeng* 68:170–173.
Strauch, E., et al. (1991) *Mol Microbiol* 5: 289–298.
Takano, E., et al. (1992) *Mol Microbiol* 6:2797–2804.
Takano, E., et al. (2000) *J. Biol. Chem.* 275:11010–11016.
Waki, M., et al. (1997) *J Bacteriol* 16:5131–5137
Wright, F., and Bibb, M. J. (1992) *Gene* 113:55–65.
Yamada, Y. (1999) Auto regulatory factors and regulation of antibiotic production in *Streptomyces.* In *Microbial signalling and communication.* England, R., Hobbs, G., Bainton, N., and Roberts, D. McL. (eds.) Cambridge: the Society for General Microbiology, pp. 177–196.
Yamada, Y., et al. (1987) *J Antibiot* 40:496–504.

All of the above references (and any later editions thereof) are hereby incorporated by reference in their entirety, individually and for all purposes.

The invention claimed is:

1. A method of modifying an antibiotic-producing strain of *Streptomyces coelicolor* to increase antibiotic production in said strain, the method comprising functionally deleting in said strain the scbA gene by introducing a deletion, stop codon or frameshift into the coding sequence of said gene, wherein before said introduction said scbA gene encodes a polypeptide having the amino acid sequence of SEQ ID NO: 17.

2. The method of claim 1, wherein the strain is *S. coelicolor* A3(2).

3. A modified strain of *Streptomyces coelicolor*, the modified strain having a functional deletion of the scbA gene, said functional deletion being effected by introducing a deletion, stop codon or frameshift into the coding sequence of said gene, whereby production of at least one antibiotic in said modified strain is increased compared to a wild-type strain of *Streptomyces coelicolor*, wherein before said introduction said scbA gene encodes a polypeptide having the amino acid sequence of SEQ ID NO: 17.

4. The strain of claim 3, which is a modified strain of *S. coelicolor* A3(2).

5. A method for identifying *Streptomyces* species in which antibiotic production is increased by the functional deletion of the scbA gene of *S. coelicolor* or a homolog thereof, said scbA gene having a nucleotide sequence which:
   (a) is the complement of nucleotides 2142–1199 of SEQ NO: 19; and/or
   (b) encodes a polypeptide having the amino acid sequence of SEQ ID NO: 17; and said homologue having a nucleotide sequence which has at least 90% sequence homology to the complement of nucleotides 2142–1199 of SEQ ID NO: 19;

the method comprising functionally deleting the scbA gene of *S. coelicolor* or said homolog thereof in an antibiotic-producing strain of a *Streptomyces* species by introducing a deletion, stop codon or frameshift into the coding sequence of said gene, the effect of said deletion on increasing said antibiotic production in said antibiotic-producing strain being unknown, said species being other than *S. virginiae* and *S. griseus*, culturing said strain under conditions suitable for the production of antibiotic, and determining whether antibiotic production in said strain is increased.

6. The method of claim 5, wherein said sequence identity is at least 95%.

7. A method for producing an antibiotic comprising culturing the modified *Streptomyces coelicolor* strain of claim 3 under conditions suitable for production of antibiotics.

8. The method of claim 7, further comprising purifying the antibiotic from the culture.

9. The method of claim 8, further comprising formulating the purified antibiotic as a pharmaceutical.

* * * * *

SEQUENCE LISTING

```
<160> NUMBER OF SEQ ID NOS: 19

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaccacgtsc csggcatg                                                    18

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtcctgstgg ccsgtsacsc gsac                                             24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccagcaggt gggcgacctg ac                                               22

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcgcccgg tcctgcttgg ccatg                                            25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 5
tatccagctg accgggaacg cgtc                                              24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atcgcccggt cctgcttggc catg                                              24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aagtagaggg ctcccttggt ca                                                22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
caaaactact gcttcgggca tg                                                22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctgcaccctg gtccggtgga ca                                                22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atcgcccggt cctgcttggc catg                                              24

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
catctgcagc gtgatcgtgg cagcttggta g                                  31

<210> SEQ ID NO 12
<211> LENGTH: 401
<212> TYPE: DNA
<213> ORGANISM: Streptomyces coelicolor

<400> SEQUENCE: 12
gggcaggacg gcggtgaccg agaaccggtc accgcccttc ggtatccagc tgaccgggaa   60
cgcgtcctgc accctggtcc ggtggacaag cgccatcgga accggcaatg cggtttgttc   120
gatcgagttg gcatcggacg cagaattgat caaaactact gcttcgggca tgggtccccc   180
ccaggaatca tgtgatgccg agctgttctg tatgcgcgaa cgttaagata cagactgagc   240
ggttttttt ctatccttcc cggggagac atgaacaagg aggcaggcat ggccaagcag     300
gacccgggcga tccgcacgcg gcagacgatc ctggacgccg cggcgcaggt cttcgagaag  360
cagggctacc aagctgccac gatcacggag atcctcaagg t                      401

<210> SEQ ID NO 13
<211> LENGTH: 401
<212> TYPE: DNA
<213> ORGANISM: Streptomyces coelicolor

<400> SEQUENCE: 13
accttgagga tctccgtgat cgtggcagct tggtagccct gcttctcgaa gacctgcgcc   60
gcggcgtcca ggatcgtctg ccgcgtgcgg atcgcccggt cctgcttggc catgcctgcc   120
tccttgttca tgtctccccc gggaaggata gaaaaaaaac cgctcagtct gtatcttaac   180
gttcgcgcat acagaacagc tcggcatcac atgattcctg gggggaccc atgcccgaag    240
cagtagtttt gatcaattct gcgtccgatg ccaactcgat cgaacaaacc gcattgccgg   300
ttccgatggc gcttgtccac cggaccaggg tgcaggacgc gttcccggtc agctggatac   360
cgaagggcgg tgaccggttc tcggtcaccg ccgtcctgcc c                      401

<210> SEQ ID NO 14
<211> LENGTH: 57
<212> TYPE: PRT
<213> ORGANISM: Streptomyces coelicolor

<400> SEQUENCE: 14

Met Pro Glu Ala Val Val Leu Ile Asn Ser Ala Ser Asp Ala Asn Ser
 1               5                  10                  15

Ile Glu Gln Thr Ala Leu Pro Val Pro Met Ala Leu Val His Arg Thr
            20                  25                  30

Arg Val Gln Asp Ala Phe Pro Val Ser Trp Ile Pro Lys Gly Gly Asp
        35                  40                  45

Arg Phe Ser Val Thr Ala Val Leu Pro
    50                  55

<210> SEQ ID NO 15
<211> LENGTH: 37
<212> TYPE: PRT
<213> ORGANISM: Streptomyces coelicolor

<400> SEQUENCE: 15

Met Ala Lys Gln Asp Arg Ala Ile Arg Thr Arg Gln Thr Ile Leu Asp
 1               5                  10                  15

Ala Ala Ala Gln Val Phe Glu Lys Gln Gly Tyr Gln Ala Ala Thr Ile
            20                  25                  30

Thr Glu Ile Leu Lys
        35

<210> SEQ ID NO 16
<211> LENGTH: 215
<212> TYPE: PRT
<213> ORGANISM: Streptomyces coelicolor

<400> SEQUENCE: 16

Met Ala Lys Gln Asp Arg Ala Ile Arg Thr Arg Gln Thr Ile Leu Asp
 1               5                  10                  15

Ala Ala Ala Gln Val Phe Glu Lys Gln Gly Tyr Gln Ala Ala Thr Ile
            20                  25                  30

Thr Glu Ile Leu Lys Val Ala Gly Val Thr Lys Gly Ala Leu Tyr Phe
        35                  40                  45

His Phe Gln Ser Lys Glu Glu Leu Ala Leu Gly Val Phe Asp Ala Gln
    50                  55                  60

Glu Pro Pro Gln Ala Val Pro Glu Gln Pro Leu Arg Leu Gln Glu Leu
65                  70                  75                  80

Ile Asp Met Gly Met Leu Phe Cys His Arg Leu Arg Thr Asn Val Val
                85                  90                  95

Ala Arg Ala Gly Val Arg Leu Ser Met Asp Gln Gln Ala His Gly Leu
            100                 105                 110

Asp Arg Arg Gly Pro Phe Arg Arg Trp His Glu Thr Leu Leu Lys Leu
        115                 120                 125

Leu Asn Gln Ala Lys Glu Asn Gly Glu Leu Leu Pro His Val Val Thr
    130                 135                 140

Thr Asp Ser Ala Asp Leu Tyr Val Gly Thr Phe Ala Gly Ile Gln Val
145                 150                 155                 160

Val Ser Gln Thr Val Ser Asp Tyr Gln Asp Leu Glu His Arg Tyr Ala
                165                 170                 175

Leu Leu Gln Lys His Ile Leu Pro Ala Ile Ala Val Pro Ser Val Leu
            180                 185                 190

Ala Ala Leu Asp Leu Ser Glu Glu Arg Gly Ala Arg Leu Ala Ala Glu
        195                 200                 205

Leu Ala Pro Thr Gly Lys Asp
    210                 215

<210> SEQ ID NO 17
<211> LENGTH: 313
<212> TYPE: PRT
<213> ORGANISM: Streptomyces coelicolor

<400> SEQUENCE: 17

Met Pro Glu Ala Val Val Leu Ile Asn Ser Ala Ser Asp Ala Asn Ser
 1               5                  10                  15

Ile Glu Gln Thr Ala Leu Pro Val Pro Met Ala Leu Val His Arg Thr
            20                  25                  30

Arg Val Gln Asp Ala Phe Pro Val Ser Trp Ile Pro Lys Gly Gly Asp
        35                  40                  45

Arg Phe Ser Val Thr Ala Val Leu Pro His Asp Pro Phe Phe Ala
    50                  55                  60

Pro Val His Gly Asp Arg His Asp Pro Leu Leu Ile Ala Glu Thr Leu
65                  70                  75                  80

```
Arg Gln Ala Ala Met Leu Val Phe His Ala Gly Tyr Gly Val Pro Val
                85                  90                  95

Gly Tyr His Phe Leu Met Thr Leu Asp Tyr Thr Cys His Leu Asp His
            100                 105                 110

Leu Gly Val Ser Gly Glu Val Ala Glu Leu Glu Val Glu Val Ala Cys
            115                 120                 125

Ser Gln Leu Lys Phe Arg Gly Gln Pro Val Gln Gly Gln Val Asp
        130                 135                 140

Trp Ala Val Arg Arg Ala Gly Arg Leu Ala Ala Thr Gly Thr Ala Thr
145                 150                 155                 160

Thr Arg Phe Thr Ser Pro Gln Val Tyr Arg Arg Met Arg Gly Asp Phe
                165                 170                 175

Ala Thr Pro Thr Ala Ser Val Pro Gly Thr Ala Pro Val Pro Ala Ala
                180                 185                 190

Arg Ala Gly Arg Thr Arg Asp Glu Asp Val Val Leu Ser Ala Ser Ser
            195                 200                 205

Gln Gln Asp Thr Trp Arg Leu Arg Val Asp Thr Ser His Pro Thr Leu
        210                 215                 220

Phe Gln Arg Pro Asn Asp His Val Pro Gly Met Leu Leu Leu Glu Ala
225                 230                 235                 240

Ala Arg Gln Ala Ala Cys Leu Val Thr Gly Pro Ala Pro Phe Val Pro
                245                 250                 255

Ser Ile Gly Gly Thr Arg Phe Val Arg Tyr Ala Glu Phe Asp Ser Pro
                260                 265                 270

Cys Trp Ile Gln Ala Thr Val Arg Pro Gly Pro Ala Ala Gly Leu Thr
            275                 280                 285

Thr Val Arg Val Thr Gly His Gln Asp Gly Ser Leu Val Phe Leu Thr
        290                 295                 300

Thr Leu Ser Gly Pro Ala Phe Ser Gly
305                 310

<210> SEQ ID NO 18
<211> LENGTH: 262
<212> TYPE: PRT
<213> ORGANISM: Streptomyces coelicolor

<400> SEQUENCE: 18

Met Arg Ala His Gly Thr Arg Tyr Gly Arg Pro Leu Glu Gly Lys Thr
1               5                   10                  15

Ala Leu Val Thr Gly Gly Ser Arg Gly Ile Gly Arg Gly Ile Ala Leu
                20                  25                  30

Arg Leu Ala Ala Asp Gly Ala Leu Val Ala Val His Tyr Gly Ser Ser
            35                  40                  45

Glu Ala Ala Ala Arg Glu Thr Val Glu Thr Ile Arg Ser Ser Gly Gly
        50                  55                  60

Gln Ala Leu Ala Ile Arg Ala Glu Leu Gly Val Val Gly Asp Ala Ala
65                  70                  75                  80

Ala Leu Tyr Ala Ala Phe Asp Ala Gly Met Gly Glu Phe Gly Val Pro
                85                  90                  95

Pro Glu Phe Asp Ile Leu Val Asn Asn Ala Gly Val Ser Gly Ser Gly
            100                 105                 110

Arg Ile Thr Glu Val Thr Glu Glu Val Phe Asp Arg Leu Val Ala Val
        115                 120                 125

Asn Val Arg Ala Pro Leu Phe Leu Val Gln His Gly Leu Lys Arg Leu
```

```
            130                 135                 140
Arg Asp Gly Gly Arg Ile Ile Asn Ile Ser Ser Ala Ala Thr Arg Arg
145                 150                 155                 160

Ala Phe Pro Glu Ser Ile Gly Tyr Ala Met Thr Lys Gly Ala Val Asp
                165                 170                 175

Thr Leu Thr Leu Ala Leu Ala Arg Gln Leu Gly Glu Arg Gly Ile Thr
            180                 185                 190

Val Asn Ala Val Ala Pro Gly Phe Val Glu Thr Asp Met Asn Ala Arg
        195                 200                 205

Arg Arg Gln Thr Pro Glu Ala Ala Ala Leu Ala Ala Tyr Ser Val
    210                 215                 220

Phe Asn Arg Ile Gly Arg Pro Asp Asp Ile Ala Asp Val Val Ala Phe
225                 230                 235                 240

Leu Ala Ser Asp Asp Ser Arg Trp Ile Thr Gly Gln Tyr Val Asp Ala
                245                 250                 255

Thr Gly Gly Thr Ile Leu
            260

<210> SEQ ID NO 19
<211> LENGTH: 4346
<212> TYPE: DNA
<213> ORGANISM: Streptomyces coelicolor

<400> SEQUENCE: 19
gtcgacgacg cgtcgggtt cgacgccgac gcggtactcg ttcccggcca ccgggcaccg      60
ggtctgcgct cgatgaccga ccgcatcgag gacgtcggct ggcggctcct gatagtgagc     120
ggccccgccg gcggcacgca catcgacgtc catctcccac tgcgccccg gaaagtgagc      180
accgcaccgc ggacgtgacg ccatgggagg gccacgtccg cggacggatc accctggct     240
tcggccgaag gcttccgcgt ggtccgccgc ccagatgcgg aacggcctgg cgggccggcc    300
cgtcacttcc cgcacggtcg gcacgacctg cgccttggcc ccgcccgct gccgctcggc     360
gctctccagg aacgcgtcgg cgacgggcct cggatacttc cggagcatct gctcgcgcgc    420
cgcctccagc cccagctcct cgaaacgcag tgaccgcccc agcacctcgg agagccgcgc    480
cgtctgctgc ctggcggtga tcgcctcggg cccggacagc gcgtacgccc gtccctcgtg    540
gccgggccgg gtcagtgccc tgaccgccac ttccgcgatg tcgcgcggat cgacgcaggc    600
aaccggggac gtgccgtaca gcgcgcggac cacgccgtcg gaccggatgg cgggcgccca    660
ggacagcgtg ttggacatga aggtcctggc ccgcaggaag gtccagtcta gcccggactc    720
gcgtacggcc cgctcgttct cgcgctgccg ccgcgtgatg aagtcgtccg cgcccggttc    780
ccccaccgcg agcatggaca gcttcaccag gtgccggacg ccggcctcgc gcgccgccgc    840
cgcgaaacgc tcgtcgtccg gctcggtggc actgttcgtg acgaggaacg ccgcccgcac    900
cccgttgagg gccggtcca ggccccgggcg gtcggcgtac tcgcccgcgc agacctcgac    960
gttcgggccg gtgacggtca cccgttccgg ccgccgggcg aggactctga cgggaccggt   1020
ccgggccagc aggtgggcga cctgacggcc gaccacaccg gtcacgccgg tcacaagaat   1080
cactcgggc tcctctcggg cagcgaggca ggggcgcctc gaacataca tatgagggga     1140
agggcaggat ctgccccggg gcgcgaaccg gcgatgttcg cgccccgggg ccggtgcttc   1200
agccggagaa cgcggggccg gacagcgtgg tgaggaagac gaggctgccg tcctgatgcc   1260
cggtgacccg cacggtggtc agcccgccg ccggccccgg ccggaccgtc gcctggatcc    1320
agcacgggct gtcgaactcc gcgtaccgga cgaaccgggt gccgccgatc gacggcacga   1380
```

```
agggcgccgg accggtcacg aggcacgccg cctgccgtgc cgcctcgagc agcagcatgc   1440
ccggtacgtg gtcgttgggg cgctggaaga gggtcgggtg actggtgtcc acccgcagtc   1500
gccacgtgtc ctgctgcgaa ctcgccgaca ggaccacgtc ctcgtcgcgg gtgcgaccgg   1560
cgcgcgccgc gggcacgggc gcggtcccgg gcaccgatgc ggtgggagtc gcgaagtcgc   1620
cgcgcatccg ccggtagact tgaggactgg tgaagcgcgt cgtggcagtc cccgtggcag   1680
cgagccgtcc ggcgcggcgc acggcccagt ccacctgtcc ctgtacgggc tgcccgccgc   1740
ggaacttcag ctgggaacag gccacttcca cctccagctc cgcgacctcg cccgacacgc   1800
cgaggtggtc gaggtggcag gtgtagtcca gcgtggccat caggaagtgg tagcccaccg   1860
gcacgccgta gccggcgtgg aagacgagca tcgccgcctg acgcagggtc tcggcgatca   1920
gcagcggatc gtgtcggtcc ccgtggaccg gtgcgaagaa cgggtggtcg tggggcagga   1980
cggcggtgac cgagaaccgg tcaccgccct tcggtatcca gctgaccggg aacgcgtcct   2040
gcaccctggt ccggtggaca agcgccatcg gaaccggcaa tgcggtttgt tcgatcgagt   2100
tggcatcgga cgcagaattg atcaaaacta ctgcttcggg catgggtccc cccaggaat   2160
catgtgatgc cgagctgttc tgtatgcgcg aacgttaaga tacagactga gcggtttttt   2220
ttctatcctt cccgggggag acatgaacaa ggaggcaggc atggccaagc aggaccgggc   2280
gatccgcacg cggcagacga tcctggacgc gcgggcgcag gtcttcgaga agcagggcta   2340
ccaagctgcc acgatcacgg agatcctcaa ggtggccggg gtgaccaagg gagccctcta   2400
cttccacttc cagtccaagg aagaactggc gctgggcgtc ttcgacgccc aggaaccacc   2460
acaggccgtt ccggagcaac ccctccggct gcaagaactc atcgacatgg gcatgttgtt   2520
ctgtcaccgc ttgcgcacga acgtcgtggc ccgggccggc gtgcgcctct ccatggacca   2580
gcaggcgcac ggtctcgatc gccgaggacc cttccgtcgc tggcacgaga cactcctgaa   2640
gctgctgaac caggccaagg agaacggtga gttgctgccc catgtggtca ccaccgactc   2700
ggccgatctc tacgtgggca cgttcgccgg gatacaggtc gtgtcccaga cggtcagcga   2760
ctaccaggac ctcgaacacc gctacgcgct gctgcagaag cacatcctgc cgccatcgc   2820
ggttccctcc gtgctggccg cgctcgatct ctccgaggag cgcggagcac gcctcgcggc   2880
cgaactggca ccgaccggga aggactgacc gccgaagcgc ccgcaccgga taccgacccg   2940
ccgtgcccga gcggccgacc ggggccgcct acgggcccgg cggcgggccc gtaggtctgc   3000
cctgcgtacc gaagcgtggc gggtcagaga atcgttccgc ctgtggcatc gacgtactgg   3060
ccggtgatcc accgtgagtc gtcggaggcc agaaaggcca ccacgtcggc gatgtcgtcg   3120
ggtctgccga tgcggttgaa cacggagttg gcggccagtg ccgcggccgc ctcgggggtc   3180
tgccgccgcc gtgcgttcat gtccgtctcc acgaaacccg gcgccaccgc gttgaccgtg   3240
atccccgtt cccccagttg cctggccagg gcgagcgtga gcgtgtccac cgcacccttg   3300
gtcatcgcgt atccgatgga ctcggggaac gcgcgccggg tcgcggcaga cgagatgttg   3360
atgatccgcc cgccgtcgcg cagtcgtttc agtccgtgct ggaccaggaa cagcggtgcc   3420
cggacgttga cggcgaccag tcggtcgaag acctcctcgg tgacttccgt gatccgtccc   3480
gagccgctga cgcccgcgtt gttcaccagg atgtcgaact cgggcggcac tccgaactcg   3540
cccatcccgg cgtcgaacgc cgcgtagagc gcggccgcgt cacccacgac gccgagttcg   3600
gcccggatgg ccaacgcctg tccgccgctg ctccggatgg tctcgacggt ctctcgcgcc   3660
gccgcctcgc tgctgccgta gtggactgcc acgagcgccc cgtccgcggc cagccgcagg   3720
```

```
                                                                -continued
gcgataccgc gtccgatgcc ccggcttccc ccggtcacca gggcggtctt gccctccagc    3780
ggtcttccat acctcgtccc atgtgcacgc atatcagccc ccgccgtgcg tgagcgaccc    3840
atggcggccg ctcggccgtt cgaatcgacg gtcacagcct acctgtgacc gcgtcagacg    3900
gggccggagt ggcccggttg gacggctggg gccagatcgg gcggcgcgca cggggaaccg    3960
gcgccggtca ggggtcaggg gtcgccggga ccgcccaggc cggtcagggc accgaccgga    4020
tcgaggtcgg gcgtgccacg cggccaccag tcctcgcggc ccagctccga ctcgtacgcg    4080
taccagagcc cggtccggcc gagtctgagc tggacgtggc cgcgcgggtg ggtgaggcgg    4140
ttgcgccagg ggcggaaggc ggggaggtcg gcggcgagca tcatggggcg ggcgcggtcg    4200
aaacggccgg ccggcgggtc ccagggctcc tccaggacgt ctagacccgc caacccgccc    4260
tgccgccagg cggcgacggc ccgcgccagc tccgccgtgt cgcgtccggc ggccgaggcg    4320
agcgacgcgt agagcgcgcg ggtacc                                        4346
```